United States Patent [19]

Arai et al.

[11] 4,237,217

[45] Dec. 2, 1980

[54] SILVER HALIDE EMULSION CONTAINING TWO-EQUIVALENT MAGENTA COUPLER

[75] Inventors: Atsuaki Arai, Minami-ashigara; Keisuke Shiba, Shizuoka; Minoru Yamada, Minami-ashigara; Nobuo Furutachi, Minami-ashigara; Kotaro Nakamura, Minami-ashigara, all of Japan

[73] Assignee: Fuji Photo Film Co., Ltd., Minami-ashigara, Japan

[21] Appl. No.: 853,051

[22] Filed: Nov. 17, 1977

Related U.S. Application Data

[63] Continuation of Ser. No. 585,899, Jun. 11, 1975, abandoned.

[30] Foreign Application Priority Data

Jun. 11, 1974 [JP] Japan .................................. 49-66378

[51] Int. Cl.[3] .............................. G03C 7/00; G03C 1/40
[52] U.S. Cl. .................................... 430/387; 430/472; 430/474; 430/476; 430/555; 430/558; 430/551; 430/505
[58] Field of Search ........................... 96/74, 100, 96/36, 56.5; 430/555, 558, 474, 387, 551, 505

[56] References Cited

U.S. PATENT DOCUMENTS

| 2,322,027 | 6/1943 | Jelley et al. | 96/74 |
|---|---|---|---|
| 3,311,476 | 3/1967 | Loria | 96/100 |
| 3,379,529 | 4/1968 | Porter et al. | 96/36 |
| 3,615,506 | 10/1971 | Abbott et al. | 96/100 |

OTHER PUBLICATIONS

Research Disclosure, Apr. 1973 #10828, pp. 47-53, Photographic Elements Containing Image Dye-Providing Layer Units.

Mason, Processing Chemistry, 1966, pp. 254-261, Focal Press, N. Y., N. Y.

*Primary Examiner*—J. Travis Brown
*Attorney, Agent, or Firm*—Sughrue, Rothwell, Mion, Zinn and Macpeak

[57] ABSTRACT

A two-equivalent magenta coupler in which the coupling position is substituted with a sulfonamido group, and capable of forming a magenta color image on coupling with an oxidation product of an aromatic primary amine developing agent, and a silver halide color photographic light-sensitive material having at least one silver halide emulsion layer on a support and containing the two-equivalent magenta coupler.

34 Claims, 1 Drawing Figure

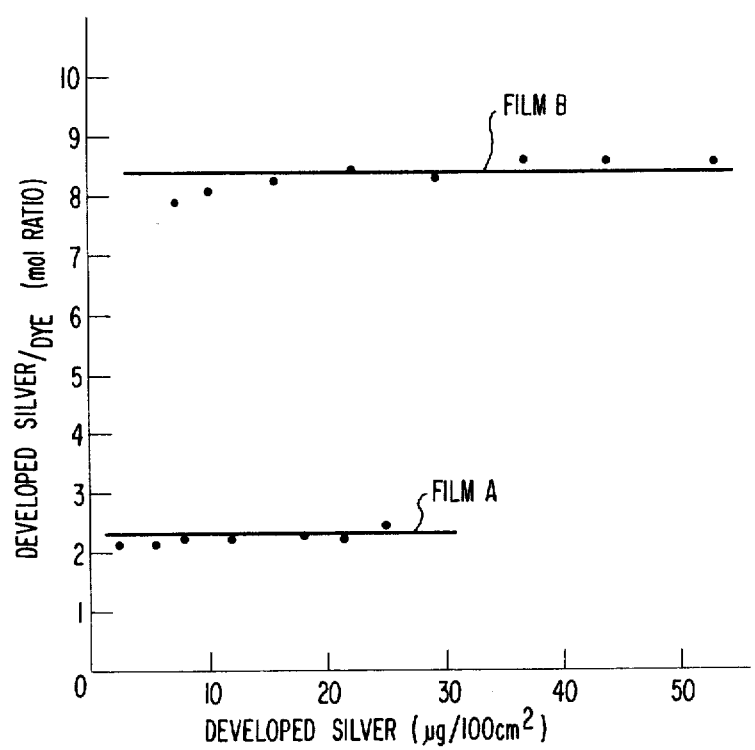

SILVER HALIDE EMULSION CONTAINING TWO-EQUIVALENT MAGENTA COUPLER

This is a continuation of application Ser. No. 585,899, filed June 11, 1975, abandoned.

BACKGROUND OF THE INVENTION

1. Field of the Invention

The present invention relates to color photography and more particularly, it relates to a novel class of two-equivalent magenta couplers which are suitable for use in silver halide color photographic light-sensitive materials.

2. Description of the Prior Art

It is known that, by color development of a silver halide color photographic material, a color developing agent of aromatic primary amine type is oxidized and reacts with a coupler to form a dye, such as indophenols, indoanilines, indamines, azomethines, phenoxazines, phenazines and the like, thus forming a color image. In this type, the subtractive color process is ordinarily used for color reproduction and yellow, magenta and cyan color images are formed, which are, respectively, the complementary colors of blue, green and red. For example, a coupler of the acylacetanilide or dibenzoylmethane type is used for forming a yellow color image, a coupler of the pyrazolone, cyanoacetophenone or indazolone type is used for forming a magenta color image and a coupler of the phenol type, such as a phenol and a naphthol, is used for forming a cyan color image.

In one of the most preferred embodiments of color photographic light-sensitive materials, the dye image forming couplers are incorporated into a silver halide emulsion. These couplers which are incorporated into the emulsion must be non-diffusible (diffusion resistant) in the binder matrix of the emulsion.

The color image-forming couplers of the prior art are almost all four-equivalent couplers which require theoretically four moles of silver halide as an oxidizing agent for forming one mole of the dye through the coupling reaction. On the contrary, a two-equivalent coupler having an active methylene group which is substituted with a group capable of being split off through the coupling of an oxidized product of an aromatic primary amine developing agent requires only the development of two moles of silver halide for forming one mole of the dye. Since the quantity of silver halide required for forming a dye with a two-equivalent coupler is one half of that required with an ordinary four-equivalent coupler, the two-equivalent coupler had many advantages in that a thinner light-sensitive layer can be used and the layer can be processed rapidly. In addition, the photographic properties and economy can increased through a reduction in the layer thickness.

Several attempts have been made to convert 5-pyrazolone type couplers which have been conventionally used as a magenta color forming coupler to two-equivalent couplers. For example, the 4-position of the pyrazolone is substituted with a thiocyano group as described in U.S. Pat. Nos. 3,214,437 and 3,253,924, an acyloxy group as described in U.S. Pat. No. 3,311,476, an acyloxy group as described in U.S. Pat. No. 3,419,391 a 2-triazolyl group as described in U.S. Pat. No. 3,617,291, a halogen atom as described in U.S. Pat. No. 3,522,052, and the like.

However, when these 4-position substituted pyrazolone couplers are employed, some disadvantages occur in that a remarkable color fog is produced, in that the coupling reactivity is insufficient, in that the couplers per se are chemically unstable and change into compounds which can not form dyes or in that many difficulties are encountered in the preparation thereof.

It is also known that the 4-position of the 5-pyrazolones can be substituted with an alkylthio group, an arylthio group or a heterocyclic thio group as described in U.S. Pat. No. 3,227,554. However, most these known thio-substituted pyrazolone compounds have the disadvantages that their reactivity with the oxidation products of an aromatic primary amine color developing agent is not suitable, that the mercapto compounds which are formed upon the coupling reaction have a very severe photographic effect when used in a conventional color photographic light-sensitive material, and that the couplers are chemically unstable.

SUMMARY OF THE INVENTION

Therefore, an object of the present invention is to provide a novel two-equivalent magenta color image forming coupler in which the coupling position of the magenta coupler is substituted with a group capable of being released by the coupling reaction with an oxidation product of an aromatic primary amine developing agent.

Another object of the present invention is to provide a novel two-equivalent magenta coupler which has a suitable reactivity and which is capable of forming a dye with a high yield and without forming undesired stains and fog.

Another object of the present invention is to provide a color photographic light-sensitive material having a silver halide emulsion layer containing a novel magenta color image forming coupler.

Still another object of the present invention is to provide a method whereby the amount of silver halide in the photographic emulsion layer can be reduced and the sharpness of the color image obtained is improved by the use of a novel magenta color image forming coupler.

Still another object of the present invention is to provide a color photograph having a durable color image by the use of a novel magenta color image forming coupler.

A further object of the present invention is to provide a novel two-equivalent magenta coupler which can be prepared in a simple manner and in a high yield.

A further object of the present invention is to provide a novel two-equivalent magenta coupler which has an improved conversion rate to the dye, an excellent resistance to the effects of chemical compounds and a good coupling reactivity.

A still further object of the present invention is to provide a method of forming a dye image in the presence of a novel two-equivalent magenta coupler in which the coupling position of the magenta color image forming coupler is substituted with a group capable of being released on coupling with an oxidation product of an aromatic primary amine developing agent.

A still further object of the present invention is to provide a method of forming a dye image by treating a silver halide photographic light-sensitive material with a color developer solution containing a novel two-equivalent magenta coupler in which the coupling position of the magenta color image forming coupler is substituted with a group capable of being released on coupling with an oxidation product of an aromatic primary amine developing agent.

Other objects of the present invention will be apparent from the following detailed description and examples.

These objects of the present invention are accomplished with a two-equivalent magenta coupler whose coupling position is substituted with a sulfonamido group, capable of forming a magenta color image upon coupling with an oxidation product of an aromatic primary amine developing agent and a silver halide color photographic light-sensitive material having at least one silver halide emulsion layer on a support and containing the two-equivalent magenta coupler.

BRIEF DESCRIPTION OF THE ACCOMPANYING DRAWING

The drawing is a graph showing that the molar ratios of developed silver to dye at various density stages with Film A and Film B in Example 1, respectively.

DETAILED DESCRIPTION OF THE INVENTION

More particularly, it has been found that these objects are achieved by incorporating a novel two-equivalent magenta coupler in which the coupling position of the magenta color image forming coupler is substituted with a sulfonamido group into a silver halide emulsion. Further these objects are achieved by a method of forming a dye image in which a silver halide photographic light-sensitive material is developed with a color developer solution containing the above-described two-equivalent magenta coupler.

Suitable couplers of the present invention are magenta color image forming couplers having a sulfonamido group in their coupling position. Preferred couplers are represented by the following general formulae (I) and (I).

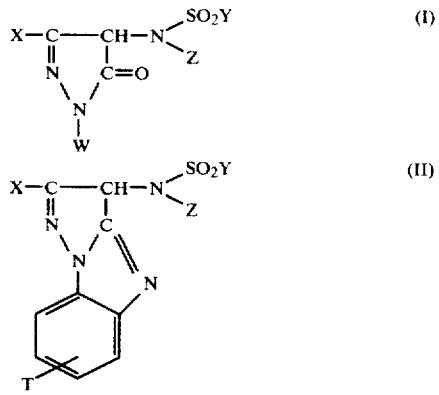

In the above general formulae, W represents a hydrogen atom or a group having 1 to 35 carbon atoms, preferably 1 to 22 carbon atoms, including a straight chain or branched chain alkyl group (e.g., a methyl, ethyl, isopropyl, tert-butyl, hexyl, dodecyl, docosyl, etc., group) an alkenyl group (e.g., an allyl β-vinylethyl, etc., group); and a cycloalkyl group (such as a cyclohexyl, norbornyl, 7,7-dialkylnorbornyl, 2-pentadecyl-7,7-dialkylnorbornyl, etc., group). These groups can be substituted with a halogen (e.g., chlorine, bromine, fluorine, etc.) or a nitro, cyano, aryl (e.g., phenyl, tolyl, methoxyphenyl, naphthyl, etc.), alkoxy (e.g., methoxy, butoxy, octyloxy, etc.), aryloxy (e.g., phenoxy, tolyloxy, naphthoxy, etc.), carboxy, alkoxycarbonyl (e.g., methoxycarbonyl, butoxycarbonyl, etc.), aryloxycarbonyl (e.g., phenoxycarbonyl, tolyloxycarbonyl, etc.), sulfo, sulfamoyl (e.g., N-methylsulfamoyl, N,N-diethylsulfamoyl, N-methyl-N-phenylsulfamoyl, etc.), carbamoyl (e.g., N-ethylcarbamoyl, N-methyl-N-decylcarbamoyl, phenylcarbamoyl, etc.), acylamino (e.g., acetamido, butyramido, benzamido, etc.), ureido (e.g., ethylureido, phenylureido, chlorophenylureido, etc.), heterocyclic (e.g., a 5- or 6-membered heterocyclic group or condensed heterocyclic group containing at least one hetero atom selected from nitrogen, oxygen and sulfur atoms, such as furyl, oxazolyl, benzothiazolyl, imidazolyl, etc.), arylsulfonyloxy (e.g., phenylsulfonyloxy, tolylsulfonyloxy, etc.) or oxo group. Specific group are, e.g., a β-cyanoethyl, β-chloroethyl, benzyl, nitrobenzyl, dichlorobenzyl, γ-(2,4-di-tert-amylphenoxy)propyl, β-phenoxyethyl, etc., group). Furthermore, W represents an aryl group having 6 to 40 carbon atoms (such as a phenyl or an α- or β-naphthyl group); an aryl group having one or more substituents such as alkyl (e.g., methyl, ethyl, octyl, etc.), alkoxy (e.g., methoxy, butoxy, octyloxy, etc.), aryloxy (e.g., phenoxy, tolyloxy, naphthoxy, etc.), alkoxycarbonyl (e.g., methoxycarbonyl, butoxycarbonyl, etc.), acylamino (e.g., acetamido, butyramido, benzamido, etc.), carbamoyl, such as alkylcarbamoyl, dialkylcarbamoyl, arylcarbamoyl, etc. (e.g., N-ethylcarbamoyl, N-methyl-N-decylcarbamoyl, phenylcarbamoyl, etc.), alkylsulfonyl (e.g., methylsulfonyl, octylsulfonyl, etc.), arylsulfonyl (e.g., phenylsulfonyl, tolylsulfonyl, etc.), alkylsulfonamido (e.g., methylsulfonamide, ethylsulfonamido, etc.), arylsulfonamido (e.g., phenylsulfonamido, etc.), dialkylsulfamoyl (e.g., N,N-diethylsulfamoyl, etc.), alkyl-arylsulfamoyl (e.g., N-methyl-N-phenylsulfamoyl, etc.), alkylthio (e.g., methylthio, octylthio, dodecylthio, etc.), arylthio (e.g., phenylthio, tolylthio, etc.), cyano, nitro, carboxy and sulfo groups or halogen atoms (e.g., chlorine, bromine, fluorine, etc.). A phenyl group in which at least one of the ortho-positions is substituted with an alkyl group, an alkoxy group or a halogen atom is particularly useful as W, since when the coupler remains in a color photographic material after development, less print-out due to the action of light or heat occur. Furthermore, W represents a heterocyclic group such as a 5-membered or 6-membered heterocyclic group or condensed heterocyclic group (for example, containing one or more nitrogen, oxygen and sulfur atoms as heteroatoms, such as pyridyl, quinolyl, furyl, benzothiazolyl, oxazolyl, imidazolyl or naphthoxazolyl group) or a substituted heterocyclic group substituted with the substituents described above for the aryl group. Furthermore, W represents a carbamoyl or thiocarbamoyl group.

T represents a hydrogen atom, a group having 1 to 22 carbon atoms and selected from an alkyl (e.g., methyl, ethyl, octyl, etc.), alkoxy (e.g., methoxy, butoxy, octyloxy, etc.), aryloxy (e.g., phenoxy, tolyloxy, naphthoxy, etc.), alkoxycarbonyl (e.g., methoxycarbonyl, butoxycarbonyl, etc.), acylamino (e.g., acetamido, butyramido, benzamido, etc.), carbamoyl (such as alkylcarbamoyl, dialkylcarbamoyl, arylcarbamoyl, etc., e.g., N-ethylcarbamoyl, N-methyl-N-decylcarbamoyl, phenylcarbamoyl, etc.), alkylsulfonyl (e.g., methylsulfonyl, octylsulfonyl, etc.), arylsulfonyl (e.g., phenylsulfonyl, tolylsulfonyl, etc.), alkylsulfonamido (e.g., methylsulfonamido, ethylsulfonamido, etc.), arylsulfonamido (e.g., phenylsulfonamido, etc.), dialkylsulfamoyl (e.g., N-N-diethylsulfamoyl, etc.), alkyl-arylsulfamoyl (e.g., N-methyl-N-phenylsulfamoyl, etc.), alkylthio (e.g., methylthio, octylthio, dodecylthio, etc.), arylthio (e.g., phenylthio, tolylthio, etc.), carboxy, sulfo, aryl (e.g., phenyl, tolyl, methoxyphenyl, naphthyl, etc.), heterocyclic (e.g., a 5- or 6-membered heterocyclic group or condensed heterocyclic group containing at least one hetero atom selected from nitrogen, oxygen and sulfur atoms, such as furyl, oxazolyl, benzathiazolyl, imidazolyl, etc.) and cyano group or a halogen atom (e.g., chlorine, bromine, fluorine, etc.).

X represents a group having 1 to 35 carbon atoms, preferably 1 to 22 carbon atoms, i.e., the same alkyl, substituted alkyl, aryl, substituted aryl, heterocyclic or substituted heterocyclic groups as described for W. Furthermore, X represents a hydrogen atom; a halogen atom (e.g., chlorine, bromine, fluorine, etc.); an alkoxycarbonyl group (e.g., a methoxycarbonyl, ethoxycarbonyl, etc., group); an aryloxycarbonyl group (e.g., a phenoxycarbonyl, tolyloxycarbonyl, etc., group); an aralkoxycarbonyl group (e.g., a benzyloxycarbonyl, etc., group); a hydroxy group; a substituted oxy group (such as an alkoxy group (e.g., a methoxy, ethoxy, decyloxy, etc., group), an aryloxy group (e.g., a phenoxy, tolyloxy, etc., group)); a mercapto group; a substituted thio group (e.g., an alkyl thio group (e.g., an ethylthio, propylthio, etc, group, an aryl thio group (e.g., a phenylthio, tolylthio, etc., group)); a carboxy group; an amino group (such as an N-alkylamino group (e.g., an N-ethylamino, N-octylamino, etc., group), a cycloalkylamino group (e.g., a cyclohexylamino, etc., group), an N,N-dialkylamino group (e.g., an N,N-dimethylamino, N-methyl-N-octylamino, etc., group), an N-alkyl-N-arylamino group (e.g., an N-methyl-N-phenylamino, etc., group), or an N-arylamino group (e.g., an N-phenylamino, N-tolylamino, etc., group)); an amido group (such as an acetamido, α-(2,4-di-tert-amylphenoxy)acetamido, α-phenoxypropionamido, 3-[(3-pentadecylphenoxy)acetamido]benxamido or benzamido group); an N-alkylacylamino group (e.g., an N-methylacetamido, etc., group); an N-arylacylamino group (e.g., an N-phenylacetamido, etc., group); a ureido group (such as an N-arylureido group (e.g., an N-phenylureido, N-tolylureido, etc., group) or an N-alkylureido group (e.g., an N-methylureido, N-octylureido, etc., growth)); an alkoxycarbonylamino group (e.g., a methoxycarbonylamino, octoxycarbonylamino, etc., group); an aryloxycarbonylamino group (e.g., a phenoxycarbonylamino, tolyloxycarbonylamino, etc., group); an alkoxythiocarbonylamino group (e.g., a methoxythiocarbonylamino, octoxythiocarbonylamino, etc., group); an aryloxythiocarbonylamino group, (e.g., a phenoxythiocarbonylamino, tolyloxythiocarbonylamino, etc., group); a thioureido group (such as an N-alkylthioureido group (e.g., an N-methylthioureido, N-octylthioureido, etc., group) or an N-arylthioureido group (e.g., an N-phenylthioureido, N-tolylthioureido, etc., group); a carbamoyl group (such as a carbamoyl, N-octadecylcarbamoyl, N,N-dihexylcarbamoyl, N-methyl-N-phenylcarbamoyl, 3-pentadecylphenylcarbamoyl, etc., group); a sulfamoyl group (e.g., a methylsulfamoyl, diethylsulfamoyl, phenylsulfamoyl, etc., group); a cycloamino group (e.g., a piperidino, a pyrrolidino, etc., group); or a guanidino group (such as a guanidino group, an N-alkylguanidino group (e.g., an N-ethylguanidino, etc., group) or an N-arylguanidino (e.g., an N-phenylguanidino, etc. group).

Y represents a group having 1 to 40 carbon atoms including an alkyl group, an aryl group, a heterocyclic group, and a group in which an alkyl, aryl or heterocyclic group is connected to an oxygen atom or a nitrogen atom which is connected to the $SO_2$ moiety. The alkyl group includes a straight chain alkyl group, a branched chain alkyl group and an alkenyl group (such as a methyl, ethyl, isopropyl, allyl, hexenyl, pentadecyl, octadecyl, tert-butyl, etc., group) and also includes an aralkyl group (such as a benzyl, phenethyl, γ-phenylpropyl, etc., group). Furthermore, the alkyl group can be substituted with a halogen atom (such as a fluorine, chlorine, bromine, etc., atom); a nitro group; a carboxy group; an alkoxy group (for example, an alkoxy group having 1 to 20 carbon atoms (e.g., a methoxy, ethoxy, octadecyloxy, etc., group)); an aryloxy group (e.g., a phenoxy, naphthoxy, etc., group); an alkylamido group (for example, an alkylamidio group having 2 to 20 carbon atoms (e.g., an acetamido, tetradecanamido, etc., group)); an arylamido group (for example, an arylamido group having 7 to 20 carbon atoms and containing an aryl group such as a phenyl, substituted phenyl, naphthyl, substituted naphthyl, etc., group); a sulfamoyl group (e.g., N-methylsulfamoyl, N,N-diethylsulfamoyl, N-methyl-N-phenylsulfamoyl, etc., group); a carbamoyl group (e.g., N-ethylcarbamoyl, N-methyl-N-decylcarbamoyl, phenylcarbamoyl, etc., group); a substituted amino group (for example, an N-alkylamino group (e.g., an N-ethylamino, N-octylamino, etc., group), an N,N-dialkylamino group (e.g., an N,N-dimethylamino, N-methyl-N-octylamino, etc., group) or an N-arylamino group (e.g., an N-phenylamino, N-tolylaino, etc., group), each having up to 20 carbon atoms); an alkylthio group (for example, an alkylthio group having 1 to 20 carbon atoms (e.g., a hexylthio, dodecylthio, etc, group)); an arylthio group (for example, an arylthio group having 6 to 20 carbon atoms (e.g., a phenylthio, 2-carboxyphenylthio, etc, group)); and the like.

Furthermore the aryl group includes a phenyl group, a naphthyl group, a substituted phenyl group and a substituted naphthyl group. The aryl group can be substituted with an alkyl group having 1 to 20 carbon atoms (e.g., a methyl, ethyl, octadecyl, etc., group); an aralkyl group (e.g., a benzyl phenethyl, etc., group); an alkenyl group (e.g., an alkyl, β-vinylethyl, etc., group), an alkoxy group (e.g., a methoxy, butoxy, octyloxy, etc., group); an aryloxy group (e.g., a phenoxy, tolyloxy, naphthoxy, etc., group); a halogen atom (for example, a fluorine, chlorine, bromine, etc., atom); a nitro group; a cyano group; a carboxy group; an alkoxycarbonyl group (e.g., a methoxycarbonyl, tetradecyloxycarbonyl, etc., group); an aryloxycarbonyl group (e.g., a phenoxycarbonyl, naphthoxycarbonyl, etc., group); an alkylamido group (for example, an alkylamido group having 2 to 20 carbon atoms (e.g., an acetamido, tetradecanamido, etc., group)); an arylamindo group (for example, an arylamido group having 7 to 20 carbon atoms and containing an aryl group such as a phenyl, naphthyl, substituted phenyl or substituted naphthyl group); a diacylamino group (for example, a phthalimido, succinimido, etc., group); a sulfamoyl group (e.g., an N-methylsulfamoyl, N,N-diethylsulfamoyl, N-methyl-N-phenylsulfamoyl, etc., group); a sulfonamido group (e.g., a methylsulfonamido, ethylsulfonamido, etc., group); an ureido group (e.g., an ethylureido, phenyliureido, chlorophenylureido, etc., group); an alkoxycarbonylamino group (e.g., a methoxycarbonylamino, octoxycarbonylamino, etc., group); an aryloxycarbonylamino group (e.g., a phenoxycarbonylamino, tolyloxycarbonylamino, etc., group); a thioureido group (e.g., a N-methylureido, N-octylureido, N-phenylureido, N-tolylureido, etc., group); an alkoxythiocarbonylamino group (e.g., a methoxythiocarbonylamino, octoxythiocarbonylamino, etc., group); an aryloxythiocarbonylamino group, (e.g., a phenoxythiocarbonylamino, tolyloxythiocarbonylamino, etc., group); a carbamoyl group (e.g., N-ethylcarbamoyl, N-methyl-N-decylcarbamoyl, phenylcarbamoyl, etc., group); a substituted amino group (for example, an N-alkylamino group (e.g., an N-ethylamino, N-octylamino, etc., group), an N,N-dialkylamino group (e.g., an N,N-dimethylamino, N-methyl-N-octylamino, etc., group) or an N-arylamino group (e.g., an N-phenylamino, N-tolylamino, etc., group), each of these groups having up to 20 carbon atoms); an alkylthio group (for example, an alkylthio group having 1 to 20 carbon atoms (e.g., a methylthio, octylthio, dodecylthio, etc., group)); an arylthio group (for example, an arylthio group having 6 to 20 carbon atoms (e.g., a phenylthio, tolylthio, etc., group); a sulfonyl group (e.g., a methylsulfonyl, octylsulfonyl, etc., group); a sulfinyl group; a carbonyl group (for example, a carbonyl group substituted with an alkyl group having 1 to 20 carbon atoms (e.g., a methylcarbonyl, dodecylcarbonyl, etc., group)); and the like.

Furthermore the heterocyclic group includes a nitrogen containing heterocyclic group (for example, a pyridyl, quinolyl or pyrrolyl group, a pyridyl or quinolyl group substituted with a substituent as described above for the aryl group), or a heterocyclic group containing two or more nitrogen atoms (for examplee, a pyrazolyl, benzotriazolyl, tetrazolyl, etc., group); an oxygen containing heterocyclic group (for example, an unsubstituted or substituted furyl or benzofuranyl group having a substituent as described above for the aryl group); a sulfur containing heterocyclic group (for example, an unsubstituted or substituted thienyl or benzo[b]thienyl group having a substituent as described above for the aryl group); and a heterocyclic group containing two or more different hetero-atoms (such as benzoaxazolyl, benzothiazolyl, and the like).

Z represents a hydrogen atom, an alkyl group, an aryl group or a heterocyclic group. The alkyl, aryl and heterocyclic groups are as above defined for Y. Preferably Z represents a hydrogen atom.

As Y, the above described alkyl group and aryl group are preferred.

The coupler represented by the general formula (I) or (II) of the present invention can combine at one of W, X, Y and T or through a divalent group derived from W, X, Y or T to form a symmetrical or unsymmetrical complex coupler (for example, a bis-compound such as Coupler (12) described hereinafter) as described by the general formulas (IIIa) to (IIId):

Cp—W'—Cp  (IIIa)

wherein W' represents a divalent moiety of the groups hereinbefore described for W; and Cp, which may be the same or different, each represents a moiety of the general formula (Ia)

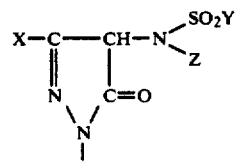

wherein X, Z and Y are as hereinbefore described;

Cp—X'—Cp  (IIIb)

wherein X' represents a divalent moiety of the groups hereinbefore described for X; and Cp, which may be the same or different, each represents a moiety of the formula (Ib) or (IIa)

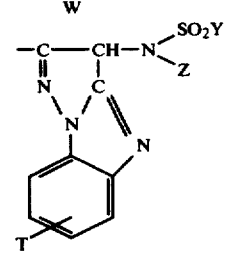

wherein T, W, Y and Z are as hereinbefore described;

Cp—Y'—Cp  (IIIc)

wherein Y' represents a divalent moiety of the groups hereinbefore described for Y; and Cp, which may be the same or different, each represents a moiety of formula (Ic) or (IIb)

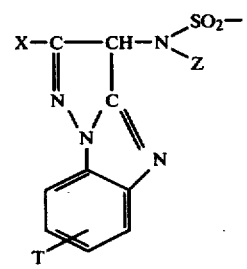

wherein T, W, X and Z are as hereinbefore described;

Cp—T'—Cp  (IIId)

wherein T' represents a divalent moiety of the groups hereinbefore described for T, and Cp, which may be the same or different, each represents a moiety of the formula (IIc)

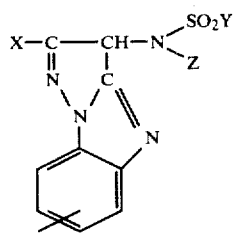

wherein X, Y and Z are as hereinbefore described.

The magenta coupler used in the present invention can provide various characteristics depending on the W, X, Y, Z and T substituents and this feature is applicable to various photographic objects. When at least one of W, X, Y and T contains a hydrophobic group of 8 or more carbon atoms, the coupler associates in a hydrophilic colloid and becomes non-diffusible in the hydrophilic colloid layer of a light-sensitive material. Such a coupler can be incorporated in a silver halide emulsion layer. When Y contains a diffusion-resistant hydrophobic group and at least one of W, X and T contains a water-solubilizing group such as a sulfo group or a carboxyl group, the coupler is non-diffusible per se but provides a diffusible dye by the oxidizing coupling reaction with an aromatic primary amine developing agent. Such a diffusible dye providing coupler is suitable for diffusion transfer color photography.

The process of forming a dye image by the oxidizing coupling reaction with an aromatic primary amine developing agent can be classified mainly into two types depending on the method of adding the coupler. In one type, the so-called "coupler-in-the-emulsion type," the coupler is incorporated in an emulsion during the production of the light-sensitive material. In the other type, the so-called "coupler-in-the-developer type," the coupler is dissolved in a developer solution and provided in the emulsion layer through diffusion during development.

The coupler used in the coupler-in-the-emulsion type must be fixed in an emulsion layer, that is, must be diffusion-resistant. If the coupler is not diffusion-resistant, the coupler migrates in a light-sensitive material and the dye is formed in the wrong light-sensitive emulsion layer, thus markedly deteriorating the color reproduction capability of the light-sensitive material.

In order to render a coupler diffusion-resistant, a group containing a hyrophobic residue of 8 to 32 carbon atoms is introduced into the coupler molecule. This residue is generally called a "ballast group." The ballast group can be combined with the coupler skeleton directly or through an imino bond, an ether bond, a carbonamido bond, a sulfonamido bond, an ureido bond, an ester bond, an imido bond, a carbamoyl bond, a sulfamoyl bond and the like.

Some examples of ballast groups are shown in the specific examples of the coupler according to the present invention set forth hereinafter. Specific examples of ballast groups are as follows:

(I) Alkyl groups and alkenyl groups e.g., $-CH_2CH\overset{\displaystyle C_2H_5}{\underset{\displaystyle C_2H_5}{\diagdown}}$, $-C_{12}H_{25}$, $-C_{16}H_{33}$, $-C_{17}H_{33}$ (II) Alkoxyalkyl groups e.g., $-(CH_2)_3O(CH_2)_7CH_3$, $-(CH_2)_3OCH_2\underset{\displaystyle C_2H_5}{\overset{\displaystyle |}{CH}}(CH_2)_8CH_3$ for example, as described in Japanese Patent Publication No. 27563/1964

(III) Alkylaryl groups

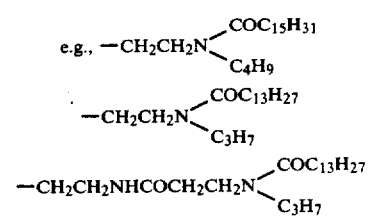

(IV) Alkylaryloxyalkyl groups

[Structural formulas of alkylaryloxyalkyl groups shown]

(V) Acylamidoalykyl groups e.g., $-CH_2CH_2N\overset{\displaystyle COC_{15}H_{31}}{\underset{\displaystyle C_4H_9}{\diagdown}}$ $-CH_2CH_2N\overset{\displaystyle COC_{13}H_{27}}{\underset{\displaystyle C_3H_7}{\diagdown}}$ $-CH_2CH_2NHCOCH_2CH_2N\overset{\displaystyle COC_{13}H_{27}}{\underset{\displaystyle C_3H_7}{\diagdown}}$ for example, as described in U.S. Pat. Nos. 3,337,344 and 3,418,129

(VI) Alkoxyaryl and aryloxyaryl groups

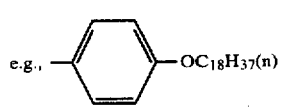

-continued

[chemical structure: —⟨phenyl⟩—O—⟨phenyl⟩—C₁₂H₂₅(n)]

(VII) Residues having both a long chain aliphatic group such as an alkyl or alkenyl group and a water solubilizing group such as a carboxy or sulfo group e.g., $-\underset{\underset{CH_2COOH}{|}}{CH}-CH=CH-C_{16}H_{33}, \quad -\underset{\underset{SO_3H}{|}}{CH}-C_{16}H_{33}$ (VIII) Alkyl groups substituted with an ester group e.g., $-\underset{\underset{COOC_2H_5}{|}}{CH}-C_{16}H_{33}(n), \quad -CH_2CH_2COOC_{12}H_{25}(n)$ (IX) Alkyl groups substituted with an aryl group or a heterocyclic group e.g., $-CH_2CH_2-$⟨phenyl⟩$-NHCOCH_2\underset{\underset{COOCH_3}{|}}{CH}-C_{18}H_{37}(n)$ $-CH_2CH_2-$⟨phenyl⟩$-N\begin{pmatrix}C=O\\C=O\end{pmatrix}C_{18}H_{37}(n)$ (X) Aryl groups substituted with an aryloxyalkoxycarbonyl group e.g., ⟨phenyl⟩$-COOCH_2\underset{\underset{C_2H_5}{|}}{CH}O-$⟨phenyl with C₅H₁₁(t), C₅H₁₁(t)⟩

A coupler dispersion of the coupler of the present invention can be advantageously prepared by dissolving the coupler into either of an organic solvent which has a high boiling point, e.g., higher than about 170° C., and is immiscible with water, a low boiling organic solvent and a water soluble organic solvent or a high boiling water-immiscible organic solvent and/or a low boiling organic solvent and/or a water soluble organic solvent.

The high boiling water-immiscible organic solvents described in U.S. Pat. No. 2,322,027 can be used as a solvent. Examples of preferred solvents are di-n-butyl phthalate, benzyl phthalate, triphenyl phosphate, tri-o-cresyl phosphate, diphenyl-mono-p-tert-butylphenylphosphate, monophenyl-di-p-tert-butylphenyl phosphate, diphenyl-mono-o-chlorophenyl phosphate, monophenyl-di-o-chlorophenyl phosphate, tri-p-tert-butylphenyl phosphate, di-p-tert-butylphenyl-mono(5-tert-butyl-2-phenylphenyl) phosphate, dioctylphthalate, dibutyl sebacate, acetyltributyl citrate, tri-tert-octyl trimelitate, n-nonylphenol, dioctylbutyl phosphate, N,N-diethyllaurylamide, 3-pentadecylphenyl ethyl ether, 2,5-di-sec-amylphenyl butyl ether, and the like.

Low boiling (e.g., lower than about 170° C.) or water soluble organic solvents which can be used together with or in place of the high boiling solvent are described in U.S. Pat. Nos. 2,801,171; 2,801,170; 2,949,360, etc. Examples of these organic solvents are as follows:

(1) Organic solvents which have a low boiling and are substantially insoluble in water such as methyl acetate, ethyl acetate, propyl acetate, butyl acetate, isopropyl acetate, ethyl propionate, secondary butyl alcohol, ethyl formate, butyl formate, nitromethane, nitroethane, carbon tetrachloride, chloroform, and the like.

(2) Water-soluble organic solvents such as methyl isobutyl ketone, β-ethoxyethylacetate, β-ethoxyethylacetate, tetrahydrofurfuryl azipate, Carbitol acetate (diethylenglycol monoacetate), methoxytriglycol acetate, methyl Cellosolve acetate, acetyl acetone, diacetonealcohol, butyl Carbitol, butyl Cellosolve, methyl Carbitol, methyl ethyl ketone, methanol, ethanol, acetonitrile, dimethylformamide, dioxane, and the like.

Preferably the solvent has a sufficiently low water content so that the solubility of coupler is not adversely affected.

A method for removing a low boiling or water soluble solvent from a coupler dispersion which comprises air-drying the cooled noodle-like dispersion or washing the cooled noodle-like dispersion continuously with water such as described in U.S. Pat. No. 2,801,171 can be employed.

For the dispersion of an oil-soluble coupler, an emulsifying homogenizer, a cooloid mill, an ultrasonic wave emulsifying apparatus, and the like are suitable. A diffusion resistant coupler having both a ballast group and a carboxylic acid group or a sulfonic acid group in the molecule is soluble in a neutral of weakly alkaline aqueous solution. The coupler can be incorporated in a photographic emulsion by adding such an aqueous solution containing the coupler to the photographic emulsion. The coupler is believed to be diffusion resistant through the formation of micelles in the hydrophilic polymer.

Specific examples of couplers according to the present invention are set forth below but the invention is not to be construed as being limited to these couplers only.

Coupler (1)

1-(2,4,6-Trichlorophenyl)-3-{3-[α-(2,4-di-tert-amylphenoxy)butyramido]benzamido}-4-phenylsulfonamido-5-oxo-2-pyrazoline Coupler (2)

1-(2,4,6-Trichlorophenyl)-3-{2-chloro-5-[(3-pentadecylphenoxy)acetamido]anilino}-4-phenylsulfonamido-5-oxo-2-pyrazoline Coupler (3)

1-(2,4,6-Trichlorophenyl)-3-{2-chloro-5-[γ-(2,4-di-tert-amylphenoxy)propylsulfamoyl]anilino}-4-ethylsulfonamido-5-oxo-2-pyrazoline Coupler (4)

1-(2,4,6-Trichlorophenyl)-3-(3,5-dicarboxyanilino)-4-(3-pentadecylphenylsulfonamido)-5-oxo-2-pyrazoline Coupler (5)

1-(2,6-Dichloro-4-tetradecyloxycarbonylphenyl)-3-(2,4-dichloroanilino)-4-phenylsulfonamido-5-oxo-2-pyrazoline Coupler (6)

1-(2,4-Dimethyl-6-chlorophenyl)-3-{3-[γ-(2,4-Ditert-amylphenoxy)butyramido]benzamido}-4-(γ-phenylpropylsulfonamido)-5-oxo-2-pyrazoline Coupler (7)

1-{2,6-Dichloro-4-[α-(2,4-di-tert-amylphenoxy)-butyramido]-phenyl}-3-(3-tert-butylbenzamido)-4-(tert-butylsulfonamido)-5-oxo-2-pyrazoline Coupler (8)

1-(2,4,6-Trichlorophenyl)-3-(2-chloro-4-tert-butyloxycarbonyl)anilino-4-{3-[α-(3-tert-butyl-4-hydroxyphenoxy)butyramido]-phenylsulfonamido}-5-oxo-2-pyrazoline Coupler (9)

1-(2,4,6-Trichlorophenyl)-3-(2-chloro-5-N,N-diethylsulfamoylanilino)-4-(1-naphthylsulfonamido)-5-oxo-2-pyrazoline Coupler (10)

1-(2,4,6-Trichlorophenyl)-3-[2-chloro-5-(2-carboxymethyl-2-nonadecenylamido)anilino]-4-benzylsulfonamido-5-oxo-2-pyrazoline Coupler (11)

1-(4-Carboxyphenyl)-3-(2-chloro-5-tetradecanamidoanilino)-4-methylsulfonamido-5-oxo-2-pyrazoline Coupler (12)

4,4'-(Tetramethylenedisulfonamido)-bis[1-(2,4,6-trichlorophenyl)-3-(2,4-dichloroanilino)-5-oxo-2-pyrazoline]

Coupler (13)

1-(2,4,6-Trichlorophenyl)-3-{3-[(2,4-di-tert-amylphenoxy)-acetamido]benzamido}-4-phenylsulfonamido-5-oxo-2-pyrazoline Coupler (14)

1-(2,4,6-Trichlorophenyl)-3-methoxy-4-phenylsulfonamido-5-oxo-2-pyrazoline

Coupler (15)

1-(2,4,6-Trichlorophenyl)-3-[(2-chloro-5-tetradecanamido)-anilino]-4-phenylsulfonamido-5-oxo-2-pyrazoline Coupler (16)

1-(2,4,6-Trichlorophenyl)-3-{3-[α-(2,4-di-tert-amylphenoxy)butyramido]benzamido}-4-(p-methylphenylsulfonamido)-5-oxo-2-pyrazoline Coupler (17)

1-(2,4,6-Trichlorophenyl)-3-{3-[(2,4-di-tert-amylphenoxy)-acetamido]benzamido}-4-methylsulfonamido-5-oxo-2-pyrazoline Coupler (18)

1-(2,6-Dichloro-4-methoxyphenyl)-3-(2,4-dichloroanilino)-4-phenylsulfonamido-5-oxo-2-pyrazoline Coupler (19)

1-(2,4,6-Trichlorophenyl)-3-(3,5-dicarboxyanilino)-4-pentadecylsulfonamido-5-oxo-2-pyrazoline Coupler (20)

1-(2,4,6-Trichlorophenyl)-3-methyl-4-(4-methylphenylsulfonamido)-5-oxo-2-pyrazoline Coupler (21)

1-(2,4,6-Trichlorophenyl)-3-(2-chloro-5-tetradecanamidoanilino)-4-methylsulfonamido-5-oxo-2-pyrazoline Coupler (22)

1-(2,4,6-Trichlorophenyl)-3-{2-chloro-5-[α-(2,4-di-tert-amylphenoxy)butyramido]anilino}-4-phenylsulfonamido-5-oxo-2-pyrazoline Coupler (23)

1-(2,4-Dichloro-6-methylphenyl)-3-(2-chloro-5-hexadecyloxycarbonylanilino)-4-(4-nitrophenylsulfonamido)-5-oxo-2-pyrazoline Coupler (24)

1-(2,4,6-Trichlorophenyl)-3-{3-[α-(2,4-di-tert-amylphenoxy)butyramido]benzamido}-4-(2-pyridylsulfonamido)-5-oxo-2-pyrazoline Coupler (25)

1-(2,4,6-Trichlorophenyl)-3-(2-chloro-5-tetradecanamidoanilino)-4-(2-benzofuranylsulfonamido)-5-oxo-2-pyrazoline Coupler (26)

1-(2,4,6-Trichlorophenyl)-3-{3-[α-(2,4-di-tert-amylphenoxy)butyramido]phenylureido}-4-phenylsulfonamido-5-oxo-2-pyrazoline Coupler (27)

1-(2,4,6-Trichlorophenyl)-3-(3,5-dicarboxyanilino)-4-ethylsulfonamido-5-oxo-2-pyrazoline Coupler (28)

1-(2,6-Dichloro-4-carboxyphenyl)-3-(2,4-dichloroanilino)-4-(3-carboxymethylphenylsulfonamido)-5-oxo-2-pyrazoline Coupler (29)

1-(2,4,6-Trichlorophenyl)-3-{3-[α-(2,4-di-tert-amylphenoxy)-butyramido]benzamido}-4-(N-ethyl-phenylsulfonamido)-5-oxo-2-pyrazoline Coupler (30)

1-(2,6-Dichloro-4-methoxyphenyl)-3-{3-[α-(2,4-di-tert-amylphenoxy)butyramido]benzamido}-4-phenylsulfonamido-5-oxo-2-pyrazoline Coupler (31)

1-(2,4,6-Trichlorophenyl)-3-[[N-Acetyl{2-chloro-5-[α-(2,4-di-tert-amylphenoxy)butyramido]}anilino]]-4-ethylsulfonamido-5-oxo-2-pyrazoline Coupler (32)

2-n-Heptadecyl-3-phenylsulfonamido-3H-pyrazolo[1,5-a]-benzimidazole

Coupler (33)

2-{3-[α-(2,4-di-tert-amylphenoxy)butyramido]benzamido}-3-phenylsulfonamido-3H-pyrazolo[1,5-a]benzimidazole The magenta couplers of the present invention in which the coupling position is substituted with a sulfonamido group can be prepared, in general, by reacting a magenta coupler having an amino group in the coupling position with various kinds of sulfonyl halides according to the following reaction scheme:

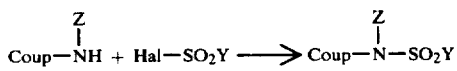

in which Y and Z each has the same meaning as defined previously, "Hal" represents a halogen atom such as a chlorine atom, "Coup" represents a four equivalent magenta dye forming coupler residue and the

is connected to the coupling position.

Magenta couplers having an amino group in their coupling positions which are employed as a starting material for preparation of the magenta coupler of the present invention are relatively unstable under neutral conditions and tend to form yellow or orange dyes and thus, these compounds are usually stored as a salt of a strong acid (for example, as the hydrochloride, sulfate, etc.), a salt of stannic chloride and the like and can be used in the reaction. Of these compounds, 4-amino-5-oxo-2-pyrazolines can be easily prepared by the method described in U.S. Pat. No. 3,419,391. That is, a four equivalent 5-oxo-2-pyrazoline magenta coupler is nitrosolated at the 4-position of the coupler with an appropriate nitrosolating agent, for example, sodium nitrite, isoamyl nitrite, etc. and then the nitroso group is reduced by an appropriate method (for example, a hydrogenation with hydrogen using palladium-carbon as a catalyst, a chemical reduction using stannous chloride, etc.).

The reaction between a 4-amino-5-oxo-2-pyrazoline and a substituted sulfonyl halide can be carried out at a temperature of about 0° to 100° C. in an inert solvent for the substituted sulfonyl halide. In a preferred embodiment, the reaction is conducted at a temperature of 0° to 40° C. and in a carboxylic acid solvent (for example, acetic acid, propionic acid, etc.), a halogenated hydrocarbon solvent (for example, methylene chloride, chloroform, carbon tetrachloride, etc.) or an aprotic polar solvent (for example, pyridine, quinoline, dimethylformamide, dimethylsulfoxide, etc.). An appropriate agent for removing hydrogen halide can be advantageously used as a catalyst in the reaction. Suitable compounds such as triethylamine, diazabiscyclo [2,2,2]-octane, sodium acetate, and the like can be effectively used.

In order to suppress the formation of colored dye which is by-produced from a 4-amino-5-oxo-2-pyrazoline, the starting material, it is preferred that a dropwise addition of the agent for removing the hydrogen halide be controlled sufficiently slowly and that the reaction be conducted under an inert gas atmosphere, other than in the presence of oxygen. Also the pyrazolobenzimidazoles represented by the general formula (II) and other magenta couplers can be prepared in a similar manner.

Typical synthesis examples of the compounds of the present invention are illustrated below. Unless otherwise indicated herein, all parts, percents, ratios and the like are by weight.

SYNTHESIS EXAMPLE 1

Preparation of
1-(2,4,6-Trichlorophenyl)-3-{3-[(2,4-di-tert-amylphenoxy)acetamido]-benzamido}-4-phenylsulfonamido-5-oxo-2-pyrazoline [Coupler (13)]

10 g of 1-(2,4,6-Trichlorophenyl)-3-{3-[(2,4-di-tert-amylphenoxy)acetamido]benzamido}-4-amino-5-oxo-2-pyrazoline stannic chloride salt, which was prepared by the method described in U.S. Pat. No. 3,419,391, was dissolved in 100 ml of chloroform and 2.7 g of phenylsulfonyl chloride was added dropwise to the solution under nitrogen gas. To the mixture, a solution of 1.5 g of triethylamine dissolved in 10 ml of chloroform was gradually added dropwise with stirring at 10° to 30° C. The addition was controled so that a remarkable orange color in the reaction mixture did not occur. After the reaction, the chloroform was distilled off under a reduced pressure. To the residue, 200 ml of ethyl acetate was added and the solution was washed with water several times. The ethyl acetate solution was dried with anhydrous sodium sulfate, condensed and crystallized from a mixture of acetonitrile and ethyl acetate (1:1 in volume ratio) to obtain 3.5 g of Coupler (13). The melting point was 223° to 225° C.

Elemental Analysis

Calculated for $C_{40}H_{42}N_5SO_6Cl_3$; H:5.08%, C:58.1%, N:8.46%; Found; H:5.10%, C:57.93%, N:8.54%.

SYNTHESIS EXAMPLE 2

Preparation of
1-(2,4,6-Trichlorophenyl)-3-{3-[α-(2,4-di-tert-amylphenoxy)butyramido]benzamido}-4-phenylsulfonamido-5-oxo-2-pyrazoline [Coupler (1)]

15 g of 1-(2,3,6-trichlorophenyl)-3-{3-[α-(2,4-di-tert-amylphenoxy)butyramido]benzamido}-4-amino-5-oxo-2-pyrazoline stannic chloride salt, which was prepared by the method described in U.S. Pat. No. 3,419,391, was dissolved in 200 ml of chloroform and 3.6 g of phenylsulfonyl chloride was added to the solution. A chloroform solution containing 2 g of triethylamine was added and treated in the same manner as described in Synthesis Example 1, and the residue obtained was crystallized from a mixture of hexane and ethyl acetate (10:1 by volume ratio) to obtain 4.3 g of Coupler (1). The melting point was 142° to 144° C.

Elemental Analysis

Calculated for $C_{42}H_{46}N_5SO_6Cl_3$; H:5.39%, C: 59.10%, N:8.20%; Found; H:5.37%, C: 58.74%, N:8.19%.

SYNTHESIS EXAMPLE 3

Preparation of
1-(2,4,6-Trichlorophenyl)-3-methoxy-4-phenylsulfonamido-5-oxo-2-pyrazoline [Coupler (14)]

9.5 g of 1-(2,4,6-trichlorophenyl)-3-methoxy-4-amino-5-oxo-2-pyrazoline hydrochloride was dissolved in 150 ml of acetic acid and 8 g of phenylsulfonyl chloride was added. To the mixture, a solution of 4.55 g of triethylamine dissolved in 80 ml of chloroform was gradually added dropwise at 10° to 30° C. over a six hour period with stirring under nitrogen gas. After the starting material was consumed, the acetic acid was distilled off under a reduced pressure. The residue was treated with a mixture of hexane and ethyl acetate (5:1 in volume ratio) and the deposited orange crystals were removed by filtration. The filtrate was sufficiently cooled to obtain 4.5 g of Coupler (14). The melting point was 168° to 170° C.

Elemental Analysis

Calculated for $C_{16}H_{12}N_3O_4SCl_3$: H: 2.59%, C: 42.8%, N: 9.37%; Found; H: 2.60%, C: 42.8%, N: 9.34%.

The couplers of the present invention can be clearly distinguished from conventionally known two equivalent magenta couplers described above in their chemical structures. Further the couplers of the present invention have the features that they have high chemical stabilities and that the synthesis thereof is very easy as is set forth in the above synthesis examples.

A cyan color image forming coupler having a two equivalent property in which the 4-position of a phenol or a naphthol is substituted with a sulfonamido group is described in U.S. Pat. No. 3,737,316. Also, as a releasable group other than the sulfonamido group in the 4-position of a phenol or a naphthol, a diacylamino group, a halogen atom, a sulfo group, a thiocyano grop, an acyloxy group, an aryloxy group, and the like are known. However, when such a releasable atom or group is introduced into the coupling position of a magenta coupler, the coupler does not exhibit the properties which the coupler of the present invention sufficiently fulfills. It is understood that a great difference in properties between a cyan coupler skelton and a magenta coupler skelton exists. Therefore, it is an extremely surprising and unexpected that superior properties can be obtained by introducing a sulfonamido group into the coupler position of a magenta coupler.

The coupler of the present invention is a two equivalent coupler which theoretically requires only two equivalents of silver halide, an an oxidizer, for forming one molecule of a dye. The required silver halide can be reduced to about half of that required using a prior art four equivalent pyrazolone type coupler, thus not only having the silver halide contained in a light-sensitive material and reducing the production cost of the light-sensitive material, but also reducing the light scattering due to the silver halide grains and improving the sharpness of the image.

The magenta coupler used in the present invention can be converted into an azomethine dye in a high yield by the oxidizing coupling reaction using an exposed silver halide as an oxidizer. Some of the four equivalent couplers used in the prior art have a low conversion yield into the dye, since the leuco dye as an intermediate product undergoes side reactions such as azine ring formation. On the contrary, the magenta coupler used in the present invention can be converted into an azomethine dye with a high yield, since the reaction does not proceed through such a reactive intermediate product. Consequently, in the color photographic light-sensitive material according to the present invention, it is possible to reduce the quantity of the magenta forming coupler, to reduce the content of the silver halide and to reduce the thickness of the emulsion layer. Thus, it is easy to reduce the cost of the light-sensitive material, to improve the sharpness and to promote development.

The magenta coupler used in the present invention has generally a strong coupling activity for an oxidized aromatic primary amine color developing agent and rapidly removes the oxidized product of the developing agent formed during color development, so that the development of a silver halide emulsion is accelerated.

In the magenta coupler used in the present invention, the process of forming a dye is completed in a color developing bath and it is not necessary to use thereafter a bleaching bath containing a strong oxidizing agent such as potassium ferricyanide or potassium bichromate. Thus, a treatment with a blixing bath containing a silver complex salt forming agent and a weak oxidizing agent such as a ferric chelate of ethylenediamine tetraacetic acid (EDTA) or a bleaching bath containing a ferric salt such as ferric chloride is possible and, consequently, it is easy to shorten the overall time for the color processings as well as to solve the problem of environmental pollution in processing solution discharge.

The magenta coupler used in the present invention in which the coupling position is substituted is inactivated by carbonyl compounds such as aldehydes and ketones to a lesser extent, while the coupling-position-unsubstituted magenta coupler used in the prior art, in particular, in an emulsion layer is changed into a compound of low color forming reactivity such as a methylol or methylenebis compound by formaldehyde in the air, and thus often does not provide sufficient color forming property during color development. One feature of the color photographic light-sensitive material according to the present invention is that the material is hardly influenced by such chemical materials.

The coupling-position-substituted magenta coupler used in the present invention has the advantages, when used for conventional color photographic light-sensitive materials as described in the Examples, that stability during the passage of time is high in an emulsion layer and, in particular, color formation is reduced to a lesser extent even after the passage of time at low temperature under high humidity, as compared with the above described known couplers. In a color photographic light-sensitive material, the stability of the film after production and on storage is one of the most important factors in the assessment of the character itself. Moreover, it has been found that a color developed dye image formed from the magenta coupler of the present invention has superior heat resistance than that formed from coupling-position-unsubstituted couplers and, even in comparison with the foregoing known coupler having a 4-position substituent on the same pyrazolone nucleus, the coupler of the present invention has a higher heat resistance.

The two equivalent coupler of the present invention can be used in an appropriate combination with a compound selected from a magenta coupler, for example, as decribed in U.S. Pat. Nos. 2,439,098; 2,369,489; 2,600,788; 3,558,319; 2,311,081; 3,419,391; 3,214,437; 3,006,759; 2,725,292; 3,408,194; 2,908,573; 3,519,429; 3,615,506; 3,432,521; 3,152,896; 3,062,653; 3,582,322; 2,801,171 and 3,311,476, British Pat. No. 956,261, Japanese Patent Publication Nos. 2016/1969; and 19032/1971; Japanese Patent Application Open To Public Inspection Nos. 74027/1974; 13041/1975; 131448/1974; 11163/1974; 60233/1975 and 74028/1974, etc., a magenta colored coupler, for example, as described in U.S. Pat. Nos. 2,983,608; 2,455,170; 2,725,292; 3,005,712; 3,519,429 and 2,688,539, British Pat. Nos. 800,262 and 1,044,778 and Belgian Pat. No. 676,691, etc., a so-called DIR coupler capable of releasing a compound imagewise inhibiting development during development, for example, a monothio type coupler described in U.S. Pat. Nos. 3,227,550 and 3,227,554 and British Pat. No. 953,454, an o-aminophenyl azo type coupler described in U.S. Pat. No. 3,148,062, a coupler described in Japanese Patent Publication No. 8750/1972 and German Patent Application (OLS) No. 2,163,811, etc., and a hydroquinone capable of releasing a compound inhibiting development during development, for example, as described in U.S. Pat. No. 3,297,445 and British Pat. No. 1,058,606, etc.

Two or more of the above described compounds such as magenta couplers and the like can be incorporated in the same layer or the same compound can be incorporated in two or more layers, in order to achieve the characteristics required in a photographic light-sensitive material.

In general, the coupler of the present invention can be coated on a supporting an amount of about $1 \times 10^{-4}$ to $5 \times 10^{-3}$ mole/m$^2$, preferably $3 \times 10^{-4}$ to $2 \times 10^{-3}$ mole/m$^2$. The coupler of the present invention can be also used in a developer solution. In such case a suitable amount of the coupler ranges from about 0.2 to 50 g, preferably 0.5 to 10 g, per liter of the developer solution.

The coupler of the present invention is advantageously used with a green-sensitive silver halide emulsion.

For the purpose of improving the fastness to light of the magenta dye formed in an emulsion layer or an adjacent layer thereto, or preventing yellowing or print-out of the coupler remaining in an unexposed portion or color stain, the photographic light-sensitive material used in the present invention advantageously contains a phenolic compound and/or a hydroquinone compound represented by the following general formula (IV a), (IV b), (IV c) or (V).

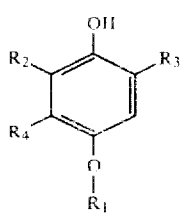
(IVa)

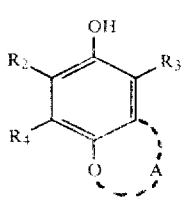
(IVb)

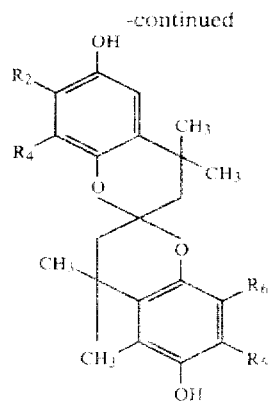
(IVc)

wherein $R_1$ can contain 1 to 20 carbon atoms and represents an alkyl group (such as a methyl group, a tert-butyl group, a hexyl group, an octyl group, a tert-octyl group, an octadecyl group, etc.); an aryl group (such as a phenyl group, etc.); an aralkyl group (such as a benzyl group, a phenethyl group, etc.); or a terpenyl group (such as a 7,7-dimethylnorbornyl group, etc.); $R_2$, $R_3$, $R_4$, $R_5$ and $R_6$, which may be the same or different, each can contain 1 to 20 carbon atoms and each can represent a hydrogen atom; an alkyl group (such as a methyl group, a tert-butyl group, a cyclopentyl group, a cyclohexyl group, an octyl group, a dodecyl group, an octadecyl group, etc.); an alkoxy group (such as a methoxy group, a butoxy group, a dodecyloxy group, etc.); an aryl group (such as a phenyl group, etc.); an aryloxy group (such as a phenoxy group, etc.); an aralkyl group (such as a benzyl group, a phenethyl group, etc.); an arlkoxy group (such as a benzyloxy group, a phenethyloxy group, etc.); an alkenyl group (such as an allyl group, etc.); an alkenoxy group (such as allyloxy group, etc.); an acylamino group (such as an acetylamino group, a benzoylamino group, etc.); a halogen atom (such as a chlorine atom, etc.); an alkylthio group (such as a dodecylthio group, etc.); an arylthio group (such as a phenylthio group, etc.); and A represents the non-metallic atoms necessary for completing a 5-membered or 6-membered ring containing a

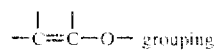 grouping (such as those forming a 6-hydroxychroman, 5-hydroxycoumaran, 3,4-ethylenedioxyphenol, etc.) and the ring can be substituted with an alkyl group (such as a methyl group, a tert-butyl group, a cyclohexyl group, an octyl group, a dodecyl group, an octadecyl group, etc.); an alkoxy group (such as a methoxy group, a butoxy group, a dodecyloxy group, etc.); an aryl group (such as a phenyl group, etc.); an aryloxy group (such as a phenoxy group, etc.); an aralkyl group (such as a benzyl group, a phenethyl group, etc.); an aralkoxy group (such as a benzyloxy group, a phenethyloxy group, etc.); an alkenyl group (such as an allyl group, etc.); an alkenoxy group (such as an allyloxy group, etc.); an N-substituted amino group (such as an alkylamino group (e.g., an N-methylamino, an N-butylamino, etc., group), a dialkylamino group (e.g., an N,N-diethylamino, etc., group), an N-alkyl-N-arylamino group (e.g., an N-methyl-N-phenylamino, N-methyl-N-(p-carboxymethyl)benzylamino, etc., group), a piperrazino group, a morpholino group, etc.); or a heterocyclic ring (such a a benzothiazolyl ring, a benzoxazolyl ring, an imidazolyl ring, an oxazolyl ring, etc.). Furthermore, the above described heterocyclic ring can be substituted with a residue forming a condensed ring. Also, the alkyl group and the aryl group as described above can be substituted with a halogein atom e.g., a chlorine, bromine, etc., atom), a hydroxyl group, a carboxy group, an alkoxycarbonyl group (e.g., a methylcarbonyl, ethoxycarbonyl, etc., group), an acyloxy group (e.g., an acetoxy, propionyloxy, etc., group), a sulfo group, a sulfonyloxy group, an amido group (e.g., an acetamido group, an ethanesulfonamido group, a benzamido grop, etc.), an alkoxy group, or an aryloxy group.

The phenolic compounds of the general formula (IV-a) in which the total number of carbon atoms of $R_1$, $R_2$, $R_3$ and $R_4$ is larger than 8, the phenolic compounds of the general formula (IV-b) in which the total number of carbon atoms of $R_2$, $R_3$, $R_4$ and A is larger than 8, and the phenolic compounds of the general formula (IV-c) have low diffusibility and hence are suitable for incorporation selectively in a specific hydrophilic colloid layer of the color photographic material. Also, phenolic compounds having a total number of carbon atoms of up to about 40 are suitable for ordinary purposes.

Particularly useful compounds of the phenolic compounds which can be used in the present invention are the 5-hydroxycoumarans and the 6-hydroxychromans which are compounds of the general formula (IV-b) where one of $R_2$ and $R_3$ is a hydrogen atom and also the 6,6'-dihydroxy-bis-2,2'-spirochromans represented by the general formula (IV-c).

The phenolic compounds which can be used in the present invention can be prepared according to the methods described in U.S. Pat. Nos. 2,535,058; 3,184,457; 3,285,937; 3,432,300; 3,457,079; 3,698,909; and 3,764,337 and the German Patent Application (OLS) Nos. 2,005,301; 2,008,376; 2,140,309; 2,146,668; and 2,165,371.

The nucleus-substituted hydroquinones which can be used in the present invention have at least one alkyl group or aryl group, bonded directly or through a bonding moiety such as —O—, —CO—, —COO—, —CON—, —SO$_2$N—, etc., to the aromatic nucleus of the hydroquinone.

The alkyl group and the aryl group can be substituted with substituents such as a halogen atom, and alkyl group, an aryl group, an alkoxy group, an aryloxy group, a carboxy group, an alkoxycarbonyl group, an aryloxycarbonyl group, an acyl group, an acyloxy group, a carbamoyl group, a sulfo group, a sulfamoyl group, a sulfonamido group, an N-alkylamino group, an N-arylamino group, acylamino group, an imido group, a hydroxyl group, etc., and these substituents themselves can be additionally substituted. Furthermore, divalent moieties corresponding to these groups can be employed to give rise to compounds in which two or more units containing hydroquinone are bonded to each other. Also, the remaining hydrogen atoms of the aromatic nucleus of the hydroquinone can be replaced by the above-described substituents as well as with halogen atoms.

Moreover, the hydroquinones which can be used in the present invention include the precursors thereof. The term "precursor" as used herein means a compound capable of releasing a hydroquinone on hydrolysis. Examples of such precursors are, for instance, hydroquinone compounds in which one or two of the hydroxyl groups thereof have been acylated, e.g., have been converted into a grouping such as

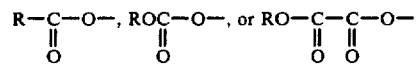

wherein R represents an aliphatic group, such as an alkyl group etc.

The nuceus-substituted hydroquinones used in the present invention include the compounds represented by the following general formula (V);

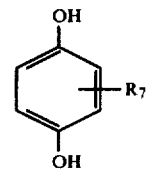

(V)

wherein $R_7$ represents an alkyl group (such as a methyl group, a tert-butyl group, an octyl group, a tert-octyl group, a dodecyl group, an octadecyl group, etc.); an aryl group (such as a phenyl group, etc.); an alkoxyl group (such as a methoxy group, a butoxy group, a dodecyloxy group, etc.); an aryloxy group (such as a phenoxy group, etc.); a carbamoyl group (such as a methylcarbamoyl group, a dibutylcarbamoyl group, an octadecylcarbamoyl group, a phenylcarbamoyl group, etc.); a sulfamoyl group (such as a methylsulfamoyl group, an octadecylsulfamoyl group, etc.); an acyl group (such as a lauroyl group, etc.); an alkoxycarbonyl group (such as methoxycarbonyl group, a dodecyloxycarbonyl group, etc.); or aryloxycarbonyl group (such as a phenyloxycarbonyl group, etc.).

Furthermore, the above described alkyl group and aryl group can be substituted with a substituent such as a halogen atom, an alkyl group, an aryl group, an alkoxy group, an aryloxy group, a carboxy group, an alkoxycarbonyl group, an aryloxycarbonyl group, an acyl group, an acyloxy group, a carbamoyl group, a sulfo group, a sulfamoyl group, a sulfonamido group, an N-alkylamino group, an N-arylamino group, an acylamino group, an imido group, and a hydroxyl group. Also one, two or three of the remaining hydrogen atoms of the aromatic nucleus of the hydroquinone can be replaced by one, two or three halogen atoms and the substituents defined for $R_7$, which can be the same or different.

Specific examples of nucleus-substituted hydroquinones which can be used in the present invention are described in e.g., U.S. Pat. Nos. 2,336,327; 2,360,290; 2,384,658; 2,403,721; 2,418,613; 2,675,314; 2,701,197; 2,704,713; 2,710,801; 2,722,556; 2,728,659; 2,732,300; 2,735,765; 2,816,028; 3,062,884 and 3,236,893; British Pat. Nos. 557,750 and 557,802; German Patent Application (OLS) No. 2,149,789; Japanese Patent Publication No. 54116/1969; and Japanese Patent Application (OPI) No. 2128/1971 as well as in *Journal of Organic Chemistry*, vol. 22, pages 772-774 (1957).

Of the above-described nucleus-substituted hydroquinones, the compounds in which the total number of carbon atoms contained in the substituents on the nucleus are 8 or more have low diffusibility and hence are suitable for incorporating selectively in a specific hydrophilic colloid layer of the color photographic material.

Particularly useful hydroquinones in the present invention are those in which the nucleus contains substituted or unsubstituted alkyl groups.

Silver halide emulsions used in the invention are usually prepared by mixing a solution of a water-soluble silver salt, for example, silver nitrate with a water-soluble halide, for example, potassium bromide, in the presence of a water-soluble polymer, for example, gelatin. In addition to silver chloride and silver bromide, mixed silver halides such as silver chlorobromide, silver iodobromide and silver chloroiodobromide can be employed in the present invention. The silver halide grains can be prepared according to conventional methods, including the so-called single jet method, double jet method and controlled double jet method. Mixtures of two or more silver halide photographic emulsions which are prepared separatedly can also be used. The silver halide grains can have a homogeneous crystal structure, a layered structure in which the interior differs from the outer layer, or can be the so-called conversion-type silver halide grains as described in British Pat. No. 635,841 and U.S. Pat. No. 3,622,318. Silver halide grains which form latent images predominantly on the surface of the grains or predominantly in the interior of the grains can also be used. These photographic emulsions are described, for example, in C. E. K. Mees & T. H. James, *The Theory of the Photographic Process*, 3rd Ed. Macmillan & Co., New York (1966); and P. Grafkides, *Chimie Photographique*, Paul Montel, Paris (1957), and can be prepared by known methods such as an ammonia method, a neutral method and an acid method.

The silver halide emulsion used in the present invention can be chemically sensitized using conventional methods. Specific examples of suitable chemical sensitizers include, for example, gold compounds such as chloroaurates and gold trichloride as described in U.S. Pat. Nos. 2,399,083; 2,540,085; 2,597,856 and 2,597,915; salts of a noble metal, such as platinum, palladium, iridium, rhodium and ruthenium, as described in U.S. Pat. Nos. 2,448,060; 2,540,086; 2,566,245; 2,566,263 and 2,598,079; sulfur compounds capable of forming silver sulfide by reacting with a silver salt, such as those described in U.S. Pat. Nos. 1,574,944; 2,410,689; 3,189,458; and 3,501,313; stannous salts, amines, and other reducing compounds such as those described in U.S. Pat. Nos. 2,487,850; 2,518,698; 2,521,925; 2,521,926; 2,694,637; 2.983,610 and 3,201,254 and the like.

Examples of the hydrophillic colloids which can be used as a binder for the silver halide grains include, for example, gelatin, colloidal albumin, casein, a cellulose derivative such as carboxymethylcellulose and hydroxyethylcellulose, a polysaccharide derivative such as agar-agar, sodium alginate and a starch derivative, a synthetic hydrophillic colloid such as polyvinyl alcohol, poly-N-vinylpyrrolidone, polyacrylic acid copolymers and polyacrylamide, or the derivatives or partially hydrolyzed products thereof. If desired, compatible mixtures of these colloids can also be employed. Of these colloids, gelatin is most commonly used. The gelatin can be replaced partially or completely by a synthetic polymer, by a so-called gelatin derivative such as those prepared by reacting or modifying the amino, imino, hydroxy or carboxy groups contained, as functional groups, in the gelatin molecule with a compound having a group capable of reacting with the above described groups, or a graft gelatin such as those prepared by grafting other polymer chains onto the gelatin molecule.

Examples of suitable compounds which can be used for the preparation of the above-described gelatin derivatives include isocyanates, acid chlorides and acid anhydrides such as those described in U.S. Pat. No. 2,614,928; acid anhydrides such as those described in U.S. Pat. No. 3,118,766; bromoacetic acids such as those described in Japanese Patent Publication No. 5514/1964; phenyl glycidyl ethers such as those described in Japanese Patent Publication No. 26845/1967; vinylsulfones such as those described in U.S. Pat. No. 3,132,945; N-allylvinylsulfonamides such as those described in British Pat. No. 861,414; maleinimides such as those described in U.S. Pat. No. 3,186,846; acrylonitriles such as those described in U.S. Pat. No. 2,594,293; polyalkylene oxides such as those described in U.S. Pat. No. 3,312,553; epoxy compounds such as those described in Japanese Patent Publication No. 26845/1967; esters such as those described in U.S. Pat. No. 2,763,639; and alkane sultones such as those described in British Patent No. 1,033,189.

A wide variety of polymers or copolymers can be employed as polymers to be grafted to gelatin, including those obtained from the so-called vinyl monomers such as acrylic acid, methacrylic acid or their derivatives, e.g., the esters, amides and nitriles thereof; or styrene. Other examples of suitable polymers are described in U.S. Pat. Nos. 2,763,625; 2,831,767; and 2,956,884; *Polymer Letters*, vol. 5, page 595 (1967); *Phot. Sci. Eng.*, vol. 9, page 148 (1965); and *J. Polymer Sci.*, part A-1, vol. 9, page 3199 (1971). Hydrophilic polymers or copolymers having a certain degree of compatibility with gelatin, such as those prepared from acrylic acid, acrylamide, methacrylamide, hydroxyalkylacrylates, hydroxyalkylmethacrylates and the like, are particularly preferred.

The photographic emulsions can be spectrally sensitized or super-sensitized, if desired, using a cyanine dye such as cyanine, merocyanine, carbocyanine or styryl dyes, individually or in combination. Spectral sensitization techniques are well known, and are described, for example, in U.S. Pat. Nos. 2,688,545; 2,912,329; 3,397,060; 3,615,635 and 3,628,964; British Pat. Nos. 1,195,302; 1,242,588 and 1,293,862; German Patent Application (OLS) Nos. 2,030,326; and 2,121,780 and Japanese Patent Publication Nos. 4936/1968; 14030/1969. The sensitizers can be chosen as desired depending on the spectral range to be sensitized, the sensitivity desired, and the like depending on the purpose and uses of the photographic materials to be sensitized.

Various kinds of conventional stabilizers or anti-fogging agents can be added to the photographic emulsions used in the present invention in order to prevent a reduction in the sensitivity or a formation of fog during preparation, storage or processing of the light-sensitive material. A wide variety of such compounds are known such as heterocyclic compounds, mercury-containing compounds, mercapto compounds or metal salts, including 4-hydroxy-6-methy-1,3,3a,7-tetrazaindene, 3-methylbenzothiazole and 1-phenyl-5-mercaptotetrazole. Examples of such compounds which can be used are described, for example, in U.S. Pat. Nos. 1,758,576; 2,110,178; 2,131,038; 2,173,628; 2,697,040; 2,304,962; 2,324,123; 2,394,198; 2,444,605-8; 2,566,245; 2,694,716; 2,697,099; 2,708,162; 2,728-663-5; 2,476,536; 2,824,001; 2,843,491; 3,052,544; 3,137,577; 3,220,839; 3,226,231; 3,236,652; 3,251,691; 3,252,799; 3,287,135; 3,326,681; 3,420,668 and 3,622,339, and British Pat. Nos. 893,428; 403,789; 1,173,609 and 1,200,188, as well as in C. E. K. Mees & T. H. James, *The Theory of the Photographic*

*Process, supra*, pages 344 to 349 and the literature references cited therein.

The photographic layers of the present invention can be hardened using conventional methods. Examples of suitable hardeners include, for example, aldehyde compounds such as formaldehyde and glutaraldehyde; ketone compounds such as diacetyl and cyclopentadione; reactive halogen-containing compounds such as bis(2-chloroethylurea), 2-hydroxy-4, 6-dichloro-1,3,5-triazine and those described in U.S. Pat. Nos. 3,288,775 and 2,732,303, and British Pat. Nos. 974,723 and 1,167,207; reactive olefin-containing compounds such as divinyl sulfone, 5-acetyl-1,3-diacryloylhexahydro-1,3,5-triazine and those described in U.S. Pat. Nos. 3,635,718 and 3,232,763; and British Pat. No. 994,869; N-methylol compounds such as N-hydroxymethylphthalimide and those described in U.S. Pat. Nos. 2,732,316 and 2,586,168; isocyanate compounds such as those described in U.S. Pat. No. 3,103,437; aziridine compounds such as those described in U.S. Pat. Nos. 3,017,280 and 2,983,611; and acid derivatives such as those described in U.S. Pat. Nos. 2,725,294 and 2,725,295; carbodiimide compounds such as those described in U.S. Pat. No. 3,100,704; epoxy compounds such as those described in U.S. Pat. No. 3,091,537; isooxazole type compounds such as those described in U.S. Pat. No. 3,321,313 and 3,543,292, etc.

The photographic emulsion used in the present invention can also contain one or more surface active agents. The surface active agent can be used as a coating aid, an emulsifier, a dispersant, a sensitizer, a agent for improving the photographic properties, an antistatic agent or an adhesion preventing agent. Suitable surface active agents include natural surface active agents such as saponin; nonionic surface active agents such as alkylene oxides, glycerols and glycidols; cationic surface active agents such as long chain alkylamines, quaternary ammonium salts, heterocyclic compounds such as pyridine and the like, phosphoniums or sulfoniums; anionic surface active agents containing an acid group such as a carboxylic acid group, a sulfonic acid group, a phosphoric acid group, a sulfuric acid ester group or a phosphoric acid ester group; amphoteric surface active agents such as amino acids, aminosulfonic acids, aminoalcohol sulfuric acid esters or aminoalcohol phosphoric acid esters. Some examples of those surface active agents which can be used are described, for example, in U.S. Pat. Nos. 2,271,623; 2,240,472; 2,288,226; 2,739,891; 3,068,101; 3,158,484; 3,201,253; 3,210,191; 3,294,540 3,415,649; 3,441,413; 3,442,654; 3,475,174; 3,545,974, German Pat. Application (OLS) No. 1,942,665; and British Patent Nos. 1,077,317 and 1,198,450, as well as Ryohei Oda et al, *Kaimenkasseizai no Gosei to sono Oyo (Synthesis and Application of Surface Active Agents)*, Maki Shoten (1964); A.M. Schwartz et al, *Surface Active Agents*, Interscience Publication Inc. (1958) and J. P. Sisley et al, *Encyclopeida of Surface Active Agents*, Vol. II, Chemical Publishing Co. (1964).

The magenta coupler of the present invention can be used in a multilayer color photographic light-sensitive material containing a yellow coupler and a cyan coupler. An open-chain diketomethylene type compound is conventionally used as a yellow coupler. Examplers of such compounds are described, for example, in U.S. Pat. Nos. 3,341,331; 3,253,924; 3,384,657; 2,778,658; 2,908,573; 3,227,550; 2,875,057 and 3,551,155, German Patent Application (OLS) No. 1,547,868, U.S. Pat. Nos. 3,265,506; 3,582,322 and 3,725,072, German Patent Application (OLS) No. 2,162,899, U.S. Pat. Nos. 3,369,895; 3,227,155; 3,447,928; 3,415,752; and 3,408,194, German Patent Application (OLS) No. 2,057,941; 2,213,461; 2,219,917; 2,261,361 and 2,263,875, and the like.

Typical yellow couplers include the following compounds:

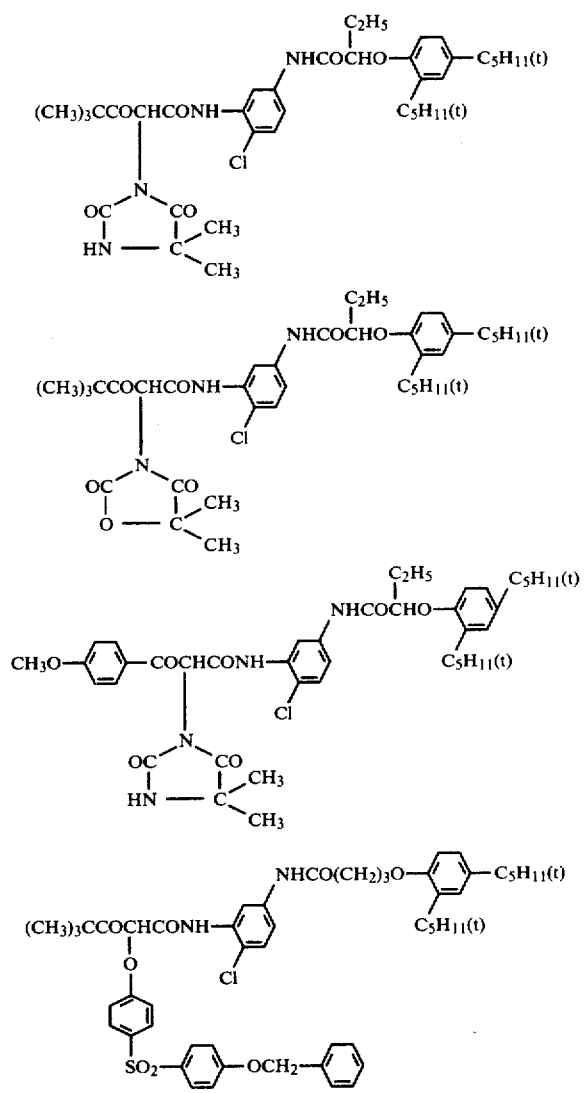

A phenol or naphthol derivative is conventionally used as a cyan coupler. Examples of such compounds are described, for example, in U.S. Pat. Nos. 2,369,929; 2,474,293; 2,908,573; 3,619,196; 3,253,294; 3,227,550; 3,419,390; 3,476,563; 2,698,794; 2,895,826; 3,311,476; 3,458,315; 2,423,730; 2,801,171; 3,046,129; 3,516,831; 2,772,162; 3,560,212; 3,582,322; 3,591,383; 3,386,301; 3,632,347; 3,652,286; 3,779,763; 2,434,272; 2,706,684; 3,034,892 and 3,583,971, German Patent Application (OLS) Nos. 2,163,811 and 2,207,468, Japanese Patent Publication Nos. 28836/1970 and 27536/1964, Japanese Patent Application No. 33238/1973 which corresponds to U.S. Pat. 3,933,500, and the like. Typical cyan couplers include the following compounds:

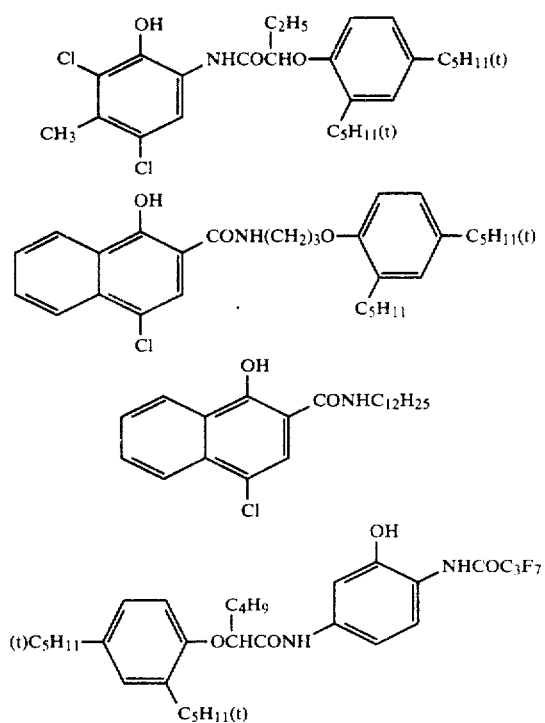

The photographic emulsion can be coated on a substantially planar material which does not undergo any severe dimensional change during processing including a rigid support such as glass, metal or ceramics, or a flexible support as desired. Representative flexible supports include those generally employed for photographic light-sensitive materials, such as a cellulose nitrate film, a cellulose acetate film, a cellulose acetate butyrate film, a cellulose acetate propionate film, a polystyrene film, a plyethylene terephthalate film, a polycarbonate film, a laminate of these polymers, a thin glass film and a paper. A baryta coated paper, a paper which is coated or laminated with an α-olefin polymer, particularly those obtained from a monomer having from 2 to 10 carbon atoms, such as polyethylene, polypropylene and ethylene-butene copolymers, and a synthetic resin film in which the ashesiveness to other polymers and the printing properties are improved by roughening the surfaces thereof, such as is described in Japanese Patent Publication No. 19068/1972, can also be used to advantage as a support. A suitable coating amount of the silver halide emulsion ranges from about $5 \times 10^{-5}$ to about $10^{-5}$ mol of silver halide per $m^2$ of the support.

These supports can be transparent or opaque, depending on the purposes of the photographic materials. Colored transparent supports which contain a dye or a pigment can also be used. Such colored supports have been utilized in X-ray films, and are described in J. SMPTE, vol. 67, page 296 (1958).

Examples of opaque supports include opaque films produced by incorporating a dye or a pigment such as titanium oxide into a transparent film or surface-treated synthetic resin films such as those described in Japanese Patent Publication No. 19068/1972 as well as intrisically opaque materials such as paper. Highly light-shielding papers and synthetic resin films containing, for example, carbon black or dyes can also be used. When the adhesion between a support and a photographic layer is unsatisfactory, a subbing layer which adheres to both of the support and the photographic layer can be provided on the support. The surfaces of the supports can also be pre-treated with a corona discharge, a UV radiation treatment, a flame treatment and the like in order to further improve the adhesiveness.

The color photographic light-sensitive materials of the present invention are, after exposure, subjected to a color processing to form dye images. This color processing includes basically a color development step, a bleaching step and a fixing step. Each step can be carried out individually or two or more steps can be combined into one step where a processing solution having these two or more functions is used. One example of such a combination both is a blix solution. Also each step can be separated into two or more steps. For example, a process comprising a color development step, a first fixing step, and a blixing step can be used. The color processing can further include a pre-hardening step, a neutralization step, a first development (black and white development) step, a stabilizing step, a washing step, and the like, if desired. The temperature of processing can be varied depending on the photographic light-sensitive material, the color processing method, and the like. In general, a temperature above 18° C. is used, although a temperature below 18° C. can be used, if desired. A temperature range of 20° to 60° C., recently 30° to 60° C., is conventionally used. Each of these processing steps need not necessarily be conducted at the same temperature.

A color developer solution is an alkaline solution having a pH of more than about 8, preferably from 9 to 12, and containing, as a developing agent, a compound, whose oxidized product is capable of forming a colored compound when reacted with a color forming agent, i.e. a color coupler. The developing agent described above includes a compound capable of developing an exposed silver halide and having a primary amino group on an aromatic ring, and a precursor which forms such a compound. Preferred typical examples of these developing agents are, for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-3-methyl-N-ethyl-N-β-ethoxyethylaniline, 4-amino-3-methoxy-N-ethyl-N-β-methoxyethylaniline, 4-amino-3-β-methanesulfonamidoethyl-N,N-diethylaniline, and the salts thereof (for example, the sulfates, the hydrochlorides, the sulfites, the p-toluene sulfonates, and the like.) Other developing agents such as those described in U.S. Pat. Nos. 2,193,015 and 2,592,364; Japanese Patent Application (OPI) No. 64933/1973; and in L. F. A. Mason Photographic Processing Chemistry, pages 226-229, Focal Press, London (1966) can be used. Also 3-pyrazolidones can be used together with these developing agents.

The color developer solution can optionally contain various additives. Typical examples of such additives include alkali agents (for example, hydroxides, carbonates or phosphates of alkali metals or ammonia); pH-adjusting agents or buffers (for example, weak acids such as acetic acid, boric acid, etc. weak bases, or the salts thereof); development accelerators (for example, various pyridinium compounds or cationic compounds such as those described in U.S. Pat. Nos. 2,648,604 and 3,671,247; potassium nitrate; sodium nitrate; condensation products of polyethylene glycol, and their derivatives such as those described in U.S. Pat. Nos. 2,533,990; 2,577,127; and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides, alkali metal iodides; nitrobenzimidazoles such as those described in U.S. Pat. Nos. 2,496,940 and 2,656,271; mercaptobenzimidazole; 5-methylbenztriazole; 1-phenyl-5-mercaptotetrazole; compounds for use in rapid processing solutions such as those described in U.S. Pat. Nos. 3,113,864; 3,342,596; 3,295,976; 3,615,522 and 3,597,199; thiosulfonyl compounds such as those described in British Patent No. 972,211; phenazine-N-oxides such as those described in Japanese Patent Publication No. 41675/1971; those described in *Kagaku Shashin Binran* (*Manual of Scientific Photography*) vol. II, pages 29-47 and the like); stain or sludge preventing agents such as those described in U.S. Pat. Nos. 3,161,513 and 3,161,514 and British Pat. Nos. 1,030,422; 1,144,481 and 1,251,558; interlayer-effect accelerators disclosed in U.S. Pat. No. 3,536,487; preservatives (for example, sulfites, bisulfites, hydroxylamine, hydrochloride, formsulfite, alkanolamine-bisulfite adducts, etc.) and the like.

After color development, the light-sensitive material is subjected to a bleaching step in a conventional manner. The bleaching step can be combined with a fixing step. Many kinds of compounds are known as a bleaching agent. Of these compounds, ferricyanides; bichromates; water-soluble cobalt (III) salts, water-soluble copper (II) salts, water-soluble quinones; nitrosophenols; complex salts of a polyvalent cation such as iron (III), cobalt (III), copper (II) and an organic acid, for example, an aminopolycarboxylic acid such as ethylenediaminetetraacetic acid, nitrilotriacetic acid, iminodiacetic acid, N-hydroxyethylethylene-diamine-triacetic acid, etc., malonic acid, tertaric acid, malic acid, diglycolic acid and dithioglycolic acid, and 2,6-dipicolinic acid; peracids such as alkylperacids, persulfates, permanganates and peroxides; hypochlorites; chlorine; bromine; and the like can be suitably used, individually or in combination. To the bleaching solution, bleaching accelerators such as those described in U.S. Pat. Nos. 3,042,520 and 3,241,966; and Japanese Patent Publication Nos. 8506/1970 and 8836/1970 and other various additives can be added.

Formation of a dye image according to the present invention can be achieved in light-sensitive materials of various forms. In one form, a light-sensitive material having a silver halide emulsion layer containing a diffusion resistant coupler on a support is processed with an alkaline developer solution containing an aromatic primary amine color developing agent to form a water-insoluble or diffusion resistant dye in the emulsion layer. In another form, a light-sensitive material having a silver halide emulsion layer in combination with a diffusion resistant coupler on a support is processed with an alkaline developer solution containing an aromatic primary amine color developing agent to form a dye soluble in an aqueous medium and diffusible and the dye is transferred to another receiving layer of a hydrophilic colloid. This is a diffusion transfer color system. In still another form, a light-sensitive material having a silver halide emulsion layer is processed with an alkaline developer solution containing an aromatic primary amine color developing agent and containing a coupler to form a water-insoluble or diffusion resistant dye in the emulsion layer. This is a coupler-in-the-developer type processing. For example, Couplers (4) and (19) can be used for the diffusion transfer color system, Couplers (9), (14), (18), (20), (27) and (28) can be used for coupler-in-the-developer system, while the other couplers hereinbefore described can be used for coupler-in-the-emulsion system.

The color photographic light-sensitive material of the present invention can be used as a color negative film, a color positive film, a color reversal film, a color printing paper and any other kind of color photographic light-sensitive material.

Advantageous results are obtained by the present invention, some of which are described in the following.

(1) The amount of silver required to provide a certain magenta color image density can be reduced, thus reducing the thickness of the light-sensitive layer containing the coupler and improving the sharpness of the image.

(2) The heat resistance of the magenta color image formed is improved by using the coupler of the present invention.

(3) A reduction in the production cost of the light-sensitive material can be achieved by using a reduced amount of silver halide.

(4) Magenta couplers which are more stable to chemical compounds such as formaldehyde or acetone are provided.

(5) Couplers having a high coupling reactivity are provided.

(6) A color image having less fog and stain and superior photographic properties is obtained.

(7) A silver halide color photographic light-sensitive material having a good stability on storage is obtained by using the coupler of the present invention.

(8) The conversion yield into the dye is improved by using the coupler of the present invention.

The present invention will be further explained by reference the following examples.

EXAMPLE 1

A mixture of 23.9 g of Coupler (1) of the greatest invention, 24 ml of dioctyl butyl phosphate and 60 ml of ethyl acetate was heated at 60° C. and the resulting solution was added to 250 ml of an aqueous solution containing 25 g of gelatin and 0.75 g of sodium dodecylbenzene sulfonate at 60° C., followed by vigorous mechanical stirring, thus obtaining a coupler dispersion. The resulting coupler dispersion was mixed with 200 g of a photographic emulsion containing $11.2 \times 10^{-2}$ mol of silver chlorobromide (silver bromide: 45 mol%; silver chloride: 55 mol%) and 20 g of gelatin and, after 10 ml of a 3% acetone solution of triethylenephosphoramide as a hardener was added thereto and the final pH was adjusted to 6.5, the mixture was coated onto a cellulose triacetate film support in a dry thickness of 4.5 microns (Film A). This film contained, per m² of the support, $1.55 \times 10^{-3}$ mol of the coupler and $6.2 \times 10^{-3}$ mol of silver chlorobromide.

For comparison, 19.6 g of 1-(2,4,6-trichlorophenyl)-3-{3-[α-(2,4-di-tert-amylphenoxy)acetamido]benzamido}-5-oxo-2-pyrazoline (Comparison Coupler A) as a corresponding comparison coupler in which the coupling position was not substituted was dispersed, in place of the above described coupler in a manner analogous to the above described coupler, mixed with 400 g of the same emulsion as described above and coated onto a film in a dry thickness of 5.1 microns (Film B). This film contained, per m² of the support, $1.57 \times 10^{-1}$ mol of the coupler and $12.6 \times 10^{-3}$ mol of silver chlorobromide.

These films were subjected to a stepwise exposure and then to the following processing:

| Color Processing Steps | Temperature (°C.) | Time |
|---|---|---|
| 1. Color Development | 21 | 12 min. |
| 2. Water Washing | " | 30 sec. |
| 3. First Fixing | " | 4 min. |
| 4. Water Washing | " | 4 min. |
| 5. Bleaching | " | 8 min. |
| 6. Water Washing | " | 4 min. |
| 7. Second Fixing | " | 4 min. |
| 8. Water Washing | " | 6 min. |

| Color Developer Solution | (pH 10.7) |
|---|---|
| Sodium Hexametaphosphate | 2 g |
| Sodium Sulfite (anhydrous) | 2 g |
| Benzyl Alcohol | 5 ml |
| Sodium Carbonate (monohydrate) | 27.5 g |
| Potassium Bromide | 0.5 g |
| Hydroxylamine Sulfate | 2.5 g |
| N-Ethyl-N-(β-methanesulfonamidoethyl)-3-methyl-4-amino-aniline Sesquisulfate | 2.5 g |
| Water to make | 1 liter |

| Fixing Solution | |
|---|---|
| Sodium Thiosulfate (hexahydrate) | 80 g |
| Sodium Sulfite (anhydrous) | 5 g |
| Borax | 6 g |
| Glacial Acetic Acid | 4 ml |
| Potassium Alum | 7 g |
| Water to make | 1 liter |

| Bleaching Solution | (pH 7.2) |
|---|---|
| Potassium Ferricyanide | 100 g |
| Potassium Bromide | 5 g |
| Boric Acid | 10 g |
| Borax | 5 g |
| Water to make | 1 liter |

After the processings, the optical density of these films was measured with green light to thus obtain the photographic properties as shown in Table 1. A clear color image was obtained having an absorption maximum of 542 mμ.

Table 1

| Film | Coupler | Coating Amount (mol/m²) Coupler | Coating Amount (mol/m²) AgX | AgX/Coupler (molar ratio) | Coating Thickness (μ) | Photographic Properties Fog | Photographic Properties Gamma | Photographic Properties Relative* Sensitivity | Photographic Properties Maximum Color Density |
|---|---|---|---|---|---|---|---|---|---|
| A | (1) | $1.55 \times 10^{-3}$ | $6.2 \times 10^{-3}$ | 4 | 4.5 | 0.03 | 3.52 | 100 | 3.59 |
| B | A | $1.57 \times 10^{-3}$ | $12.6 \times 10^{-3}$ | 8 | 5.1 | 0.02 | 2.15 | 88 | 2.48 |

*Relative sensitivity means the quantity of exposure necessary for obtaining a density of fog + 0.1.

The maximum densities are shown in Table 2, which were obtained upon processing for different periods of developing time.

Table 2

| Film | Maximum Color Density Developing Time 4 min. | 8 min. | 12 min. | 16 min. |
|---|---|---|---|---|
| A | 2.69 | 3.41 | 3.59 | 3.63 |
| B | 2.27 | 2.40 | 2.48 | 2.49 |

Furthermore, after the stepwise exposure, Film A and Film B were subjected to the above described processing steps 1 to 4 and dried, and the quantity of developed silver per unit area was measured using a fluorescent X-ray technique. Then the films were subjected to the above described processing steps 5 to 8 to obtain magenta color images. From these films, the dyes were extracted with a mixture of dimethylformamide and water in a ratio of 85:15 by volume and subjected to quantitative measurement using an absorbancy method. When the molar ratios of developed silver/dye at various density stages were calculated, Film A gave a molar ratio of 2.2 to 2.4 and Film B gave a molar ratio of 8 to 8.5 as shown in the accompanying drawing.

As is evident from the results in Table 1, the coupler of the present invention provided a higher sensitivity and gradation as well as a higher maximum color density, even when the ratio of silver halide/coupler dereases to about ½, and as is evident from the results in Table 2, the use of the coupler of the invention results in an ability to markedly shorten the developing time. The above results demonstrate that in using the coupler of the present invention, the quantity of developed silver necessary for obtaining a color image having a certain density can be reduced to a great extent. That is, the quantities of the coupler and coated silver halide necessary for obtaining a certain maximum color density can be reduced and the developing time can be shortened.

EXAMPLE 2

Using Film A and Film B as described in Example 1, the following processing was carried out:

| Color Processing Steps | Temperature (°C.) | Time |
|---|---|---|
| 1. Color Development | 30 | 4 min. |
| 2. Blixing | " | 2 min. |
| 3. Water Washing | " | 2 min. |
| 4. Stabilizing Bath | " | 2 min. |

The photographic properties of the thus obtained films are shown in Table 3.

Moreover, as to the Stabilizing Bath, two kinds of stabilizing baths, i.e., Stabilizing Bath (a) containing no formaldehyde and Stabilizing Bath (b) containing 1% of a 40% formaldehyde aqueous solution were prepared. The films were treated respectively with these baths, allowed to stand at 80° C. for one week and the decreasing ratio of the density was measured based on the initial density. The results obtained are illustrated in Table 4.

| Color Developer Solution | (pH 10.2) |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfonamidoethyl)-amino-2-methylaniline Sesquisulfate | 8 g |
| Water to make | 1 liter |
| Blixing Solution | (pH 6.9) |
| Ferric Ethylenediaminetetraacetate | 45 g |
| Ammonium Thiocyanate | 10 g |
| Sodium Sulfite | 10 g |
| Ammonium Thiosulfate (60%) | 100 ml |
| Sodium Ethylenediaminetetraacetate | 5 g |
| Water to make | 1 liter |
| Stabilizing Bath (a) | |
| Tartaric Acid | 10 g |
| Zinc Sulfate | 10 g |
| Sodium Metaborate | 20 g |
| Water to make | 1 liter |
| Stabilizing Bath (b) | |
| Tartaric Acid | 10 g |
| Zinc Sulfate | 10 g |
| Sodium Metaborate | 20 g |
| Formaldehyde (40%) | 10 ml |
| Water to make | 1 liter |

Table 3

| Film | Coupler | Photographic Property (Stabilizing Bath (a)) | | |
|---|---|---|---|---|
| | | Fog | Gamma | Maximum Color Density |
| A | (1) | 0.04 | 3.59 | 3.61 |
| B | A | 0.03 | 2.30 | 2.25 |

Table 4

| Film | Stabilizing Bath | Durability of Color Image (80° C., Storage for One Week) | | |
|---|---|---|---|---|
| | | Initial Density | | |
| | | 0.5 (%) | 1.0 (%) | 2.0 (%) |
| A | a | 12 | 9 | 7 |
| | b | 11 | 6 | 5 |
| B | a | 65 | 45 | 12 |
| | b | 13 | 9 | 7 |

The results shown in Table 3 demonstrate that the use of Film A results in a sufficient photographic property even though a strong oxidizing agent not used as in the processing of Example 1 and that Film A has superior properties to Film B. The results shown in Table 4 also demonstrate that Film A provides sufficient heat durability even though it was not subjected to a stabilizing bath treatment containing formaldehyde as in the prior art.

EXAMPLE 3

A mixture of 10 g of Coupler (30) of the present invention, 0.8 g of 2,5-di-tert-octylhydroquinone, 0.8 g of 6,6'-dihydroxy-7,7'-dimethyl-4,4,4',4'-tetramethyl-bis-2,2'-spirochroman, 10 ml of tricresyl phosphate and 30 ml of ethyl acetate was heated and disolved on a steam bath and added to an aqueous solution containing 10 g of gelatin and 0.5 g of sodium cetylsulfate, followed by vigorous mechanical stirring, thus obtaining a coupler dispersion. This coupler dispersion was mixed with 100 g of a photographic emulsion containing $4.7 \times 10^{-2}$ mol of silver chlorobromide (silver chloride 50 mol%, silver bromide: 50 mol%) and 9 g of gelatin, to which 3 ml of a 4% aqueous solution of 2-hydroxy-4,6-dichloro-s-triazine sodium salt as a hardener was then added, and the pH was adjusted to 6.3. The resulting mixture was coated onto a baryta paper resin-coated with polyethylene in a dry thickness of 1.8 microns (Film C). In this film, $4.7 \times 10^{-4}$ mol of the coupler and $1.88 \times 10^{-3}$ mol of the silver halide were coated per m² of the support.

For comparison, another coupler dispersion was prepared in the same manner as above but using 8.2 g of a 4-position unsubstituted corresponding comparison coupler, i.e., 1-(2,6-dichloro-4-methoxyphenyl)-3-{3-[α-(2,4-di-tert-amylphenoxy)-butyramido]benzamido}-5-oxo-2-pyrazoline (Comparison Coupler B), in place of the coupler of Film C, mixed with 200 g of the emulsion having the same composition and coated in a dry thickness of 3.0 microns (Film D). In this film, $7.5 \times 10^{-4}$ mol of the coupler and $6.0 \times 10^{-3}$ mol of the silver halide were coated per m² of the support.

When these samples were subjected to processing (Stabilizing Bath(a)) similar to Example 2 and the reflection density was measured with green light, the photographic properties as shown in Table 5 were obtained. A clear color image of a main wavelength of 542 mμ was obtained.

Table 5

| Film | Coupler | Coating Amount (mol/m²) | | AgX/Coupler (molar ratio) | Photographic Properties | | | |
|---|---|---|---|---|---|---|---|---|
| | | Coupler | AgX | | Fog | Gamma | Relative* Sensitivity | Maximum Color Density |
| C | (30) | $4.7 \times 10^{-4}$ | $1.88 \times 10^{-3}$ | 4 | 0.07 | 2.65 | 100 | 2.50 |
| D | B | $7.5 \times 10^{-4}$ | $6.0 \times 10^{-3}$ | 8 | 0.06 | 2.59 | 96 | 2.43 |

*as described in Example 1

It is apparent from the results in Table 5 that the light-sensitive material using the coupler of the present invention provides similar photographic properties to those of the prior art even though the coating amounts of the coupler and silver halide were decreased.

In Table 6, the light durability when the thus obtained developed films were exposed to a daylight fluorescent lamp of 30,000 luxes through a filter capable of absorbing substantially all ultraviolet light having a wavelength of 400 mμ or less for 12 days, the heat durability when these films were allowed to stand at 80° C. in the dark for one week and the humidity durability when these films were stored in the dark at 60° C. and 75% RH (Relative Humidity) for 2 weeks are shown by the decreasing ratio of density (%) based on the initial density.

Table 6

| | | Durability of Color Image (Density Decreasing Ratio %) | | | | | | | | |
|---|---|---|---|---|---|---|---|---|---|---|
| | | Fluorescent Lamp (12 days) | | | 80° C., 1 Week | | | 60° C., 75% RH 2 Weeks | | |
| Film | Coupler | 0.5* | 1.0 | 2.0 | 0.5 | 1.0 | 2.0 | 0.5 | 1.0 | 2.0 |
| C | (30) | 17 | 11 | 5 | 9 | 5 | 2 | 6 | 3 | 1 |
| D | B | 20 | 14 | 6 | 57 | 35 | 9 | 19 | 12 | 7 |

*Initial Density

It is apparent from these results that in using the coupler of the present invention, an image can be obtained which is more durable to heat, light, high temperature and high humidity as compared with using four equivalent couplers having a skelton corresponding to the coupler of the invention.

EXAMPLE 4

Onto a baryta paper resin-coated with polyethylene were coated, as a first layer, a blue-sensitive silver chlorobromide emulsion containing α-pivaloyl-α-(2,4-dioxo-5,5-dimethyloxazolidin-3-yl)-2-chloro-5-[α-(2,4-di-tert-amylphenoxy)butyramido]acetanilide in a thickness of 3.0 microns (coupler coated amount: $1.18 \times 10^{-3}$ mol/m$^2$; silver coated amount: $3.53 \times 10^{-3}$ mol/m$^2$; silver bromide: 70 mol%; silver chloride: 30 mol%) and further, as a second layer, gelatin containing 2-tert-octylhydroquinone in a thickness of 1.5 microns (hydroquinone compound coated amount: 0.05 g/m$^2$). Furthermore, a coupler dispersion was prepared in the same manner but using Coupler (22) of the present invention, in place of Coupler (30) of Example 3, added to a green-sensitive photographic emulsion having the same composition as in Example 3 and coated in a coating thickness of 1.6 microns as a third layer (coupler coated amount: $4.12 \times 10^{-4}$ mol/m$^2$; silver coated amount: $1.65 \times 10^{-3}$ mol/m$^2$), gelatin containing 2,5-di-tert-octylhydroquinone and as an ultraviolet absorber, 2-(5-chlorobenzotiazol-2-yl)-4-methyl-6-tert-butylphenol and 2-(benzotriazol-2-yl)-4-tert-butylphenol was coated in a coating thickness of 2.5 microns as a fourth layer (hydroquinone compound coated amount: 0.05 g/m$^2$; benzotriazole compound coated amount: each 0.4 g/m$^2$), a red-sensitive emulsion containing 2-[α-(2,4-di-tert-amylphenoxy)butyramido]-4,6-dichloro-5-methylphenol was coated in a coating thickness of 2.5 microns as a fifth layer (coupler coated amount: $0.98 \times 10^{-3}$ mol/m$^2$; silver coated amount: $2.94 \times 10^{-3}$ mol/m$^2$; silver bromide: 50 mol%; silver chloride: 50 mol%) and gelatin was then coated in a thickness of 1.0 micron as an uppermost layer, thus preparing a color print paper.

This color print paper was exposed through a color negative and processed in the same manner as described in Example 2. The resulting color print produced a sharp color photographic image very excellent in color reproduction and containing a megenta color image having an absorption maximum at 540 mμ.

When this color print was exposed to direct sunlight for one week, the reduction of density of the magenta color image having an initial reflection density of 1.0 was only 0.08 and, even though it was allowed to stand under high temperature and high humidity conditions, for example, at 60° C. and 75% RH for two weeks, no substantial reduction of the density was found. In addition, it was noted that the non-image area was scarcely yellowed.

EXAMPLE 5

Onto a transparent support of cellulose triacetate were coated, as a first layer, a red-sensitive silver iodobromide emulsion containing 1-hydroxy-2-tetradecylnaphthamide in a thickness of 5.0 microns (coated coupler amount: $1.8 \times 10^{-3}$ mol/m$^2$; coated silver amount: $2.12 \times 10^{-2}$ mol/m$^2$; silver iodide: 7 mol%; silver bromide: 93 mol%) and, as a second layer, gelatin containing 2,5-di-tert-octylhydroquinone in a thickness of 1.0 micron (coated hydroquinone compound amount: 0.04 g/m$^2$).

15.5 g of Coupler (13) of the present invention, 2.0 g 1-(2,4,6-trichlorophenyl)-3-[(2-chloro-5-tetradecanamido)anilino]-4-(p-methoxyphenylazo)-5-pyrazolone, 12 ml of tricresyl phosphate and 50 ml of ethyl acetate were heated at 60° C. and dissolved. The resulting solution was added to 150 ml of an aqueous solution containing 15 g of gelatin and 0.4 g of sodium dodecylbenzenesulfonate at 60° C. and the mixture was vigorously and mechanically stirred using a homogenizer to obtain a coupler dispersion. The resulting dispersion was mixed with 500 g of a green-sensitive photographic emulsion containing $3 \times 10^{-1}$ mol of silver iodobromide (silver iodide: 6 mol%; silver bromide: 94 mol%) and 30 g of gelatin, to which 5 ml of a 3% acetone solution of the sodium salt of 2-hydroxy-4,6-dichloro-s-triazine as a hardener was then added, and the pH was finally adjusted to 7.0. The emulsion was coated as a third layer (coated Coupler (13) amount: $1.52 \times 10^{-3}$ mol/m$^2$; coated colored coupler amount: $0.22 \times 10^{-3}$ mol/m$^2$; coated silver amount: $2.52 \times 10^{-2}$ mol/m$^2$) onto the above described coating in a coating thickness of 5.1 microns. Furthermore, onto the resulting coating were coated gelatin containing yellow colloidal silver and 2,5-di-tert-octylhydroquinone in a thickness of 1.5 microns (coated hydroquinone amount: 0.04 g/m$^2$), a blue-sensitive silver iodobromide photographic emulsion containing α-(p-methoxybenzoyl)-α-(5,5-dimethyl-3-hydantoinyl)-2-chloro-5-[γ-(2,4-di-tert-amylphenoxy)-butyramido]acetanilide as a fifth layer (coated coupler amount: $1.0 \times 10^{-3}$ mol/m$^2$; coated silver amount: $1.0 \times 10^{-2}$ mol/m$^2$; silver iodide: 5 mol%; silver bromide: 95 mol%) in a thickness of 5.0 microns and a protective layer of gelatin in a thickness of 1.0 micron as an uppermost layer, thus obtaining a color negative light-sensitive material.

When this film was exposed and subjected to the following processing, an excellent color negative having a high sensitivity and good gradation and image quality was obtained. The density of blue light was substantially constant and independent of the degree of exposure to green light, and the color correction was suitable.

Furthermore, even though this negative film was stored under a condition of 60% RH (relative humidity) and containing 5 ppm of formaldehyde vapor for one month and subjected to the following processing, no substantial reduction of magenta color density was observed.

| Color Processing Steps | Temperature (°C.) | Time |
|---|---|---|
| 1. Color Development | 38 | 3 min. |
| 2. Stopping | " | 1 min. |
| 3. Water Washing | " | 1 min. |
| 4. Bleaching | " | 2 min. |

| -continued | | |
|---|---|---|
| 5. Water Washing | " | 1 min. |
| 6. Fixing | " | 2 min. |
| 7. Water Washing | " | 1 min. |
| 8. Stabilizing Bath | " | 1 min. |

| Color Developer Solution | |
|---|---|
| Sodium Hydroxide | 2 g |
| Sodium Sulfite | 2 g |
| Potassium Bromide | 0.4 g |
| Sodium Chloride | 1 g |
| Borax | 4 g |
| Hydroxylamine Sulfate | 2 g |
| Ethylenediaminetetraacetic Acid | 2 g |
| N-ethyl-N-(β-hydroxyethyl)-3-methyl-4-aminoaniline Sesquisulfate Monohydrate | 4 g |
| Water to make | 1 liter |

| Stopping Solution | |
|---|---|
| Sodium Thiosulfate | 10 g |
| Ammonium Thiosulfate (70% aq. soln.) | 30 ml |
| Sodium Acetate | 5 g |
| Acetic Acid | 30 ml |
| Potassim Alum | 15 g |
| Water to make | 1 liter |

| Bleaching Solution | |
|---|---|
| Ferric Sodium Ethylenediamine-tetraacetate Dihydrate | 100 g |
| Potassium Bromide | 50 g |
| Ammonium Nitrate | 50 g |
| Boric Acid | 5 g |
| Ammonia (aqueous) | to adjust pH to 5.0 |
| Water to make | 1 liter |

| Fixing Solution | |
|---|---|
| Sodium Thiosulfate | 150 g |
| Sodium Sulfite | 15 g |
| Borax | 12 g |
| Glacial Acetic Acid | 15 ml |
| Potassium Alum | 20 g |
| Water to make | 1 liter |

| Stabilizing Bath | |
|---|---|
| Boric Acid | 5 g |
| Sodium Citrate | 5 g |
| Sodium Metaborate (tetrahydrate) | 3 g |
| Potassium Alum | 15 g |
| Water to make | 1 liter |

EXAMPLE 6

Onto a film support of polyethylene terephthalate having a thickness of 0.15 mm were coated, in order, a first layer of the n-hexyl half ester of a copolymer of vinyl methyl ether and maleic anhydride (1:1 monomer molar ratio) and having a thickness of 20 microns, a second layer of a 50% hydrolysate of polyvinyl acetate and having a thickness of 12 microns, a third layer of 4 parts by weight of acid processed gelatin and 1 part by weight of poly-N-n-butyl-6-methyl-3-vinylpyridinium bromide and having a thickness of 7 microns, a fourth layer of 10 parts by weight of rutile type titanium oxide and 1 part by weight of gelatin and having a thickness of 12 microns and then a fifth layer of 1 part by weight of carbon black and 5 parts by weight of gelatin and having thickness of 3 microns.

5.2 g of the sodium salt of Coupler (4) was dissolved with heating in a solvent mixture of 70 ml of water and 30 ml of 2-methoxyethanol and the resulting solution was added with agitation to 250 g of an aqueous solution containing 0.1 g of finely dispersed colloidal silver and 30 g of gelatin at 50° C. The resulting mixture was cooled at 5° C. and set, cut in square rods of about 5 mm in length, washed with an aqueous solution containing 0.5 g of magnesium sulfate per 1 liter at 5° C. for 5 hours, heated for redissolving at 40° C., mixed with 10 ml of a 3% methanol solution of triethylene phosphoramide and 15 ml of a 5% aqueous solution of saponin and then coated, as a sixth layer, onto the above described coating in a thickness of 7.5 microns.

After an intermediate layer of 1 part by weight of 2,5-di-tert-octylhydroquinone and 20 parts by weight of gelatin and having a thickness of 1 micron was coated onto the thus resulting coating, a green-sensitive emulsion optically sensitized with the sodium salt of anhydro-5,5'-diphenyl-3,3'-disulfopropyl-9-ethyloxacarbocyanine hydroxide was applied as an eighth layer to the intermediate layer in a thickness of 4 microns. This emulsion contained 0.28 mol of silver iodobromide (iodine content: 3 mol%; average grain size: 0.6 micron) and 72 g of gelatin per Kg. Finally a gelatin layer of 1 micron was coated as an uppermost layer to thus obtain a light-sensitive material. The resulting light-sensitive material was exposed stepwise for sensitometry through, as a cover, a sheet of cellulose triacetate of a thickness of 0.1 mm.

Between the cover sheet and the surface of the light-sensitive material, a viscous processing solution having the following composition was spread in a thickness of 0.15 mm:

| Developer Solution | |
|---|---|
| Degassed Distilled Water | 1 liter |
| Ascorbic Acid | 0.2 g |
| 4-Amino-N-ethyl-N-β-hydroxyethylaniline Sulfate | 25 g |
| Potassium Hydroxide | 35 g |
| Benzotriazole | 0.02 g |
| Hydroxyethyl Cellulose | 30 g |
| Carbon Black | 45 g |

After about 30 seconds after the spreading, a magenta image appeared gradually and it was observed from the side of polyethylene terephthalate support that the image formation was accomplished in about 4 minutes.

EXAMPLE 7

Onto a transparent support of cellulose acetate was coated a silver iodobromide photographic emulsion (coated silver amount $3 \times 10^{-3}$ mol/m$^2$; silver iodide: 5 mol%; silver bromide: 95 mol%). This sample was exposed step-wise and developed with the following developer solution to provide a silver image.

| First Developer Solution | |
|---|---|
| N-Methyl-p-aminophenol Sulfate | 5 g |
| Sodium Sulfite | 79 g |
| Hydroquinone | 2 g |
| Sodium Hydroxide | 1 g |
| Sodium Carbonate (monohydrate) | 41 g |
| Potassium Iodide (0.1% aq. soln.) | 12.5 ml |
| Potassium Bromide | 3.6 g |
| Sodium Hydroquinone Monosulfate | 4 g |
| Potassium Thiocyanate | 2 g |
| 6-Nitrobenzimidazole Nitrate | 5 ml |
| Water to make | 1 liter |

The sample was fixed and then processed with a solution containing potassium ferricyanide and potassium bromide. The sample was processed with a fogging solution and then processed with the following solution containing Coupler (28) of the present invention at 27° C. for 4 minutes followed by fixing, bleaching and fixing to provide a clear magenta dye image.

| | |
|---|---|
| Sulfuric Acid | 2 ml |
| Trisodium Phosphate (dodecahydrate) | 40 g |
| Sodium Sulfite | 5 g |
| Potassium Thiocyanate | 1.2 g |
| Potassium Iodide (0.1% aq. soln.) | 7.5 ml |
| Potassium Bromide | 0.6 g |
| 4-Amino-3-methyl-N-ethyl-N-(β-methane-sulfonamidoethyl)aniline Sesquisulfate Monohydrate | 2 g |
| Ethylenediamine | 6 ml |
| Sodium Hydroxide | 0.3 g |
| Magenta Coupler (28) | 1.7 g |
| 2-Methyl-2,4-pentanediol | 10 ml |
| Sodium Sulfate | 50 g |
| Polyoxyethylene Methyl Phenyl Ether | 0.5 g |
| Water to make | 1 liter |

While the invention has been described in detail and with reference to specific embodiments thereof, it will be apparent to one skilled in the art that various changes and modifications can be made therein without departing from the spirit and scope thereof.

What is claimed is:

1. A two-equivalent magenta image forming coupler whose coupling position is substituted with a sulfonamido group, wherein said coupler is represented by the general formula (I)

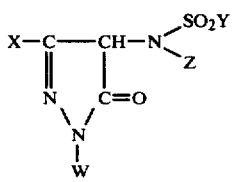

or by the general formula (II)

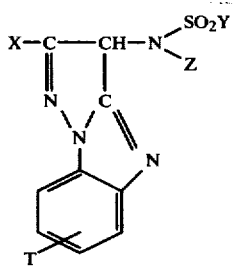

wherein W represents a hydrogen atom or a group having 1 to 35 carbon atoms selected from the group consisting of a straight chain or branched chain alkyl group; an alkenyl group; a cycloalkyl group; a substituted alkyl, substituted alkenyl or substituted cycloalkyl group, each containing one or more of a halogen atom a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a ureido group, a heterocyclic group, an arylsulfonyloxy group and an oxo group as a substituent; an aryl group; a substituted aryl group containing one or more of an alkyl group, an alkoxy group, an aryloxy group, an alkoxycarbonyl group, an acylamino group, a carbamoyl group, an alkylcarbamoyl group, a dialkylcarbamoyl group, an arylcarbamoyl group, an alkylsulfonyl group, an arylsulfonyl group, an alkylsulfonamido group, an arylsulfonamido group, a dialkylsulfamoyl group, an alkyl-arylsulfamoyl group, an alkylthio group, an arylthio group, a cyano group, a nitro group, a carboxy group, a sulfo group, and a halogen atom as a substituent; a heterocyclic group containing one or more of a nitrogen atom, an oxygen atom and a sulfur atom as a hetero atom; a substituted heterocyclic group containing the above described hetero atoms and substituted with the substituents above described for the aryl group; a carbamoyl group; and a thiocarbamoyl group;

T represents a hydrogen atom, a halogen atom or a group having 1 to 22 carbon atoms selected from the group consisting of alkyl, alkoxy, aryloxy, alkoxycarbonyl, acylamino, carbamoyl, alkylsulfonyl, arylsulfonyl, alkylsulfonamido, arylsulfonamido, dialkylsulfamoyl, alkyl-arylsulfamoyl, alkylthio, arylthio, carboxy, sulfo, aryl, heterocyclic or cyano;

X represents a group having 1 to 35 carbon atoms selected from the group consisting of the same alkyl, substituted alkyl, aryl, substituted aryl, heterocyclic or substituted heterocyclic groups as described for W; a hydrogen atom; a halogen atom; an alkoxycarbonyl group; an aryloxycarbonyl group; an aralkyloxycarbonyl group; a hydroxy group; an alkoxy group; an aryloxy group; a mercapto group; an alkylthio group; an arylthio group; a carboxy group; an amino group; an alkylamino group; a cycloalkylamino group, an N,N-dialkylamino group; an N-alkyl-N-arylamino group; an N-arylamino group; an amido group; an N-alkylacylamino group; an N-arylacylamino group; a ureido group; an N-arylureido group; an N-alkylureido group; an alkoxycarbonylamino group; an aryloxycarbonylamino group; a thioureido group; an N-alkylthioureido group; an N-arylthioureido group; an alkoxythiocarbonylamino group; an aryloxythiocarbonylamino group; a carbamoyl group; a sulfamoyl group; a piperidino group; a pyrrolidino group; a guanidino group; an N-alkylguanidino group; and an N-arylguanidino group;

Y represents a group having 1 to 40 carbon atoms selected from the group consisting of a straight chain or branched chain alkyl group; an alkenyl group; an alkyl group substituted with one or more of a halogen atom, a nitro group, a carboxy group, an alkoxy group, an alkylamido group, an arylamido group, a sulfamoyl group, a carbamoyl group, an N-alkylamino group, an N,N-dialkylamino group, an N-arylamino group, an alkylthio group, and arylthio group as substituents; an aryl group; an aryl group substituted with one or more of a halogen atom, a nitro group, a cyano group, an alkyl group, an aralkyl group, an alkenyl group, an alkoxy group, an aryloxy group, a carboxy group, an alkoxycarbonyl group, an aryloxycarbonyl group, an acyloxy group, an alkylamido group, an arylamido group, a diacylamino group, a sulfamoyl group, a sulfonamido group, an alkoxycarbonylamino group; an aryloxycarbonylamino group; a thioureido group, an alkoxythiocarbonylamino group; an aryloxythiocarbonylamino group; a carbamoyl group, an N-alkylamino group, an N,N-dialkylamino group, an N-arylamino group, an alkylthio group, an arylthio group, a sulfo group, a sulfinyl group and a carbonyl group as substituents; a heterocyclic group containing one or more of a nitrogen atom, an oxygen atom and a sulfur atom as a hetero-atom; and a substituted heterocyclic group containing the above described hetero atoms and substituted with the substituents above described for the aryl group; and Z represents a hydrogen atom or the same alkyl, substituted alkyl, aryl, substituted aryl, heterocyclic or substituted heterocyclic groups as described for Y; or represented by the general formulas (IIIa) to (IIId)

Cp—W'—Cp  (IIIa)

wherein W' represents a divalent moiety of the groups hereinbefore described for W; and Cp, which may be the same or different, each represents a moiety of the general formula (Ia)

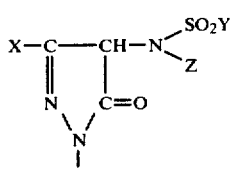
(Ia)

wherein X, Z and Y are as hereinbefore described;

Cp—X'—Cp  (IIIb)

wherein X' represents a divalent moiety of the groups hereinbefore described for X; and Cp, which may be the same or different, each represents a moiety of the formula (Ib) or (IIa)

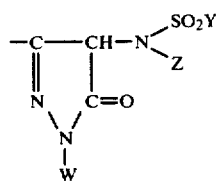
(Ib)

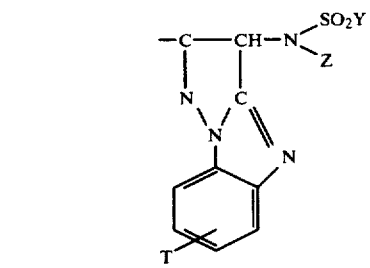
(IIa)

wherein T, W, Y and Z are as hereinbefore described;

Cp—Y'—Cp  (IIIc)

wherein Y' represents a divalent moiety of the groups hereinbefore described for Y; and Cp, which may be the same or different, each represents a moiety of formula (Ic) or (IIb)

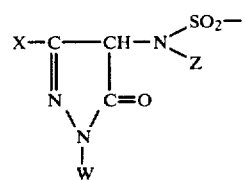
(Ic)

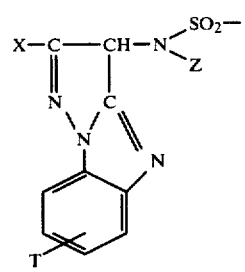
(IIb)

wherein T, W, X and Z are as hereinbefore described;

Cp—T'—Cp  (IIId)

wherein T' represents a divalent moiety of the groups hereinbefore described for T; and Cp, which may be the same or different, each represents a moiety of the formula (IIc)

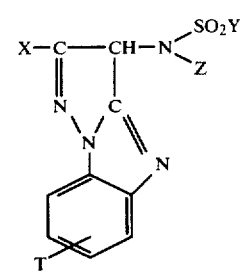
(IIc)

wherein X, Y and Z are as hereinbefore described.

2. The photographic silver halide emulsion as claimed in claim 1, wherein said silver halide emulsion contains a phenolic compound or a hydroquinone compound.

3. The photographic silver halide emulsion as claimed in claim 1, wherein said silver halide emulsion contains a phenolic compound and a hydroquinone compound.

4. A photographic material comprising a support having thereon the photographic silver halide emulsion as claimed in claim 1.

5. A photographic material comprising a support having thereon a blue-sensitive silver halide emulsion layer containing a yellow image forming coupler, a green-sensitive silver halide emulsion layer containing the emulsion as claimed in claim 1, and a red-sensitive silver halide emulsion layer containing a cyan image forming coupler.

6. The photographic silver halide emulsion as claimed in claim 1, wherein Z is a hydrogen atom.

7. The photographic silver halide emulsion as claimed in claim 6, wherein Y is an alkyl group.

8. The photographic silver halide emulsion as claimed in claim 6, wherein Y is an aryl group.

9. The photographic silver halide emulsion as claimed in claim 1, wherein said W is a phenyl group in which at least one of the ortho positions is substituted with a halogen atom, an alkyl group, an alkoxy group, a cyano group, a carboxy group, a sulfo group or an aryloxy group.

10. The photographic silver halide emulsion as claimed in claim 1, wherein X is an acylamido group, an anilino group or a phenylureido group.

11. The photographic silver halide emulsion as claimed in claim 1, wherein said two-equivalent magenta coupler is selected from the group consisting of 1-(2,4,6-Trichlorophenyl)-3-{3-[α-(2,4-di-tert-amylphenoxy)butyramido]benzamido}-4-phenylsulfonamido-5-oxo-2-pyrazoline 1-(2,4,6-Trichlorophenyl)-3-{2-chloro-5-[(3-pentadecylphenoxy)acetamido]anilino}-4-phenylsulfonamido-5-oxo-2-pyrazoline 1-(2,4,6-Trichlorophenyl)-3-{2-chloro-5-[γ-(2,4-di-tert-amylphenoxy)propylsulfamoyl]anilino}-4-ethylsulfonamido-5-oxo-2-pyrazoline 1-(2,4,6-Trichlorophenyl)-3-(3,5-dicarboxyanilino)-4-(3-pentadecylphenylsulfonamido)-5-oxo-2-pyrazoline 1-(2,6-Dichloro-4-tetradecyloxycarbonylphenyl)-3-(2,4-dichloroanilino)-4-phenylsulfonamido-5-oxo-2-pyrazoline 1-(2,4-Dimethyl-6-chlorophenyl)-3-{3-[γ-(2,4-Di-tert-amylphenoxy)butyramido]benzamido}-4-(γ-phenylpropylsulfonamido)-5-oxo-2-pyrazoline 1-{2,6-Dichloro-4-[α-(2,4-di-tert-amylphenoxy)-butyramido]-phenyl}-3-(3-tert-butylbenzamido)-4-(tert-butylsulfonamido)-5-oxo-2-pyrazoline 1-(2,4,6-Trichlorophenyl)-3-(2-chloro-4-tert-butyloxycarbonyl)anilino-4-{3-[α-(3-tert-butyl-4-hydroxyphenoxy)butyramido]-phenylsulfonamido}-5-oxo-2-pyrazoline 1-(2,4,6-Trichlorophenyl)-3-(2-chloro-5-N,N-diethylsulfamoylanilino)-4-(1-naphthylsulfonamido)-5-oxo-2-pyrazoline 1-(2,4,6-Trichlorophenyl)-3-[2-chloro-5-(2-carboxymethyl-2-nonadecenylamido)anilino]-4-benzylsulfonamido-5-oxo-2-pyrazoline 1-(4-Carboxyphenyl)-3-(2-chloro-5-tetradecanamidoanilino)-4-methylsulfonamido-5-oxo-2-pyrazoline 4,4'-(Tetramethylenedisulfonamido)-bis[1-(2,4,6-trichlorophenyl)-3-(2,4-dichloroanilino)-5-oxo-2-pyrazoline]

1-(2,4,6-Trichlorophenyl)-3-{3-[(2,4-di-tert-amylphenoxy)-acetamido]benzamido}-4-phenylsulfonamido-5-oxo-2-pyrazoline 1-(2,4,6-Trichlorophenyl)-3-methoxy-4-phenylsulfonamido-5-oxo-2-pyrazoline 1-(2,4,6-Trichlorophenyl)-3-[(2-chloro-5-tetradecanamido)-anilino]-4-phenylsulfonamido-5-oxo-2-pyrazoline 1-(2,4,6-Trichlorophenyl)-3-{3-[α-(2,4-di-tert-amylphenoxy)butyramido]benzamido}-4-(p-methylphenylsulfonamido)-5-oxo-2-pyrazoline 1-(2,4,6-Trichlorophenyl)-3-{3-[(2,4-di-tert-amylphenoxy)-acetamido]benzamido}-4-methylsulfonamido-5-oxo-2-pyrazoline 1-(2,6-Dichloro-4-methoxyphenyl)-3-(2,4-dichloroanilino)-4-phenylsulfonamido-5-oxo-2-pyrazoline 1-(2,4,6-Trichlorophenyl)-3-(3,5-dicarboxyanilino)-4-pentadecylsulfonamido-5-oxo-2-pyrazoline 1-(2,4,6-Trichlorophenyl)-3-methyl-4-(4-methylphenylsulfonamido)-5-oxo-2-pyrazoline 1-(2,4,6-Trichlorophenyl)-3-(2-chloro-5-tetradecanamidoanilino)-4-methylsulfonamido-5-oxo-2-pyrazoline 1-(2,4,6-Trichlorophenyl)-3-{2-chloro-5-[α-(2,4-di-tert-amylphenoxy)butyramido]anilino}-4-phenylsulfonamido-5-oxo-2-pyrazoline 1-(2,4-Dichloro-6-methylphenyl)-3-(2-chloro-5-hexadecyloxycarbonylanilino)-4-(4-nitrophenylsulfonamido)-5-oxo-2-pyrazoline 1-(2,4,6-Trichlorophenyl)-3-{3-[α-(2,4-di-tert-amylphenoxy)butyramido]benzamido}-4-(2-pyridylsulfonamido)-5-oxo-2-pyrazoline 1-(2,4,6-Trichlorophenyl)-3-(2-chloro-5-tetradecanamidoanilino)-4-(2-benzofuranylsulfonamido)-5-oxo-2-pyrazoline 1-(2,4,6-Trichlorophenyl)-3-{3-[α-(2,4-di-tert-amylphenoxy)butyramido]phenylureido}-4-phenylsulfonamido-5-oxo-2-pyrazoline 1-(2,4,6-Trichlorophenyl)-3-(3,5-dicarboxyanilino)-4-ethylsulfonamido-5-oxo-2-pyrazoline 1-(2,6-Dichloro-4-carboxyphenyl)-3-(2,4-dichloroanilino)-4-(3-carboxymethylphenylsulfonamido)-5-oxo-2-pyrazoline 1-(2,4,6-Trichlorophenyl)-3-{3-[α-(2,4-di-tert-amylphenoxy)-butyramido]benzamido}-4-(N-ethylphenylsulfonamido)-5-oxo-2-pyrazoline 1-(2,6-Dichloro-4-methoxyphenyl)-3-{3-[α-(2,4-di-tert-amylphenoxy)butyramido]benzamido}-4-phenylsulfonamido-5-oxo-2-pyrazoline 1-(2,4,6-Trichlorophenyl)-3-[[N-Acetyl{2-chloro-5-[α-(2,4-di-tert-amylphenoxy)butyramido]-}anilino]]-4-etjhylsulfonamido-5-oxo-2-pyrazoline 2-n-Heptadecyl-3-phenylsulfonamido-3H-pyrazolo[1,5-a]-benzimidazole 2-{3-[α-(2,4-di-tert-amylphenoxy)butyramido]benzamido}-3-phenylsulfonamido-3H-pyrazolo[1,5-a]benzimidazole 12. The photographic silver halide emulsion as claimed in claim 1, wherein Y is a straight chain or branched chain alkyl group.

13. The photographic silver halide emulsion as claimed in claim 1, wherein Y is an aryl group or an aryl group substituted with a nitro, an alkyl, an alkylamido or an arylamido group.

14. The photographic silver halide emulsion as claimed in claim 1, wherein Z is an alkyl group.

15. The photographic silver halide emulsion as claimed in claim 14, wherein Y is an aryl group or an aryl group substituted with a nitro, an alkyl, an alkylamido or an arylamido group.

16. The photographic silver halide emulsion as claimed in claim 1, wherein said two-equivalent magenta coupler has general formula (I).

17. The photographic silver halide emulsion as claimed in claim 16, wherein Z is a hydrogen atom, Y is an alkyl group or an aryl group and wherein W is a phenyl group wherein at least one of the ortho-positions is substituted with a halogen atom.

18. The photographic silver halide emulsion as claimed in claim 1, wherein said coupler is 1-(2,4,6-trichlorophenyl)-3-{3-[(2,4-di-tert-amylphenoxy)-acetamido]benzamido}-4-phenylsulfonamido-5-oxo-2-pyrazoline.

19. The photographic silver halide emulsion as claimed in claim 4, wherein said two-equivalent magenta coupler has general formula (I).

20. The photographic silver halide emulsion as claimed in claim 19, wherein Z is a hydrogen atom, Y is an alkyl group or an aryl group and wherein W is a phenyl group wherein at least one of the ortho-positions is substituted with a halogen atom.

21. The photographic silver halide emulsion as claimed in claim 20, wherein said coupler is 1-(2,4,6-trichlorophenyl)-3-{3-[(2,4-di-tert-amylphenoxy)-acetamido]benzamido}-4-phenylsulfonamido-5-oxo-2-pyrazoline.

22. The photographic material as claimed in claim 5, wherein said two-equivalent magenta coupler has general formula (I) as set forth in claim 1.

23. The photographic material as claimed in claim 22, wherein Z is a hydrogen atom, Y is an alkyl group or an aryl group and wherein W is a phenyl group wherein at least one of the ortho-positions is substituted with a halogen atom.

24. The photographic material as claimed in claim 23, wherein said coupler is 1-(2,4,6-trichlorophenyl)-3-{3-[(2,4-di-tert-amylphenoxy)-acetamido]benzamido}-4-phenylsulfonamido-5-oxo-2-pyrazoline.

25. A photographic color developer solution containing a primary aromatic amine developing agent and the two-equivalent magenta image forming coupler as set forth in claim 1.

26. The photographic color developer as claimed in claim 25, wherein said two-equivalent magenta coupler has general formula (I).

27. The photographic color developer as claimed in claim 26, wherein Z is a hydrogen atom, Y is an alkyl group or an aryl group and wherein W is a phenyl group wherein at least one of the ortho-positions is substituted with a halogen atom.

28. The photographic color developer as claimed in claim 27, wherein said coupler is 1-(2,4,6-trichlorophenyl)-3-{3-[(2,4-di-tert-amylphenoxy)-acetamido]-benzamido}-4-phenylsulfonamido-5-oxo-2-pyrazoline.

29. A method of forming a color image comprising developing an exposed photographic light-sensitive silver halide material comprising a support having thereon at least one silver halide emulsion layer with a photographic developer solution containing a primary aromatic amine developing agent in the presence of the two-equivalent magenta image forming coupler as set forth in claim 1.

30. The method as claimed in claim 29, wherein said two-equivalent magenta image forming coupler is present in said photographic light-sensitive silver halide material.

31. The method as claimed in claim 29, wherein said two-equivalent magenta image forming coupler is present in said photographic developer solution.

32. The method as claimed as claimed in claim 29, wherein said two-equivalent magenta coupler has general formula (I).

33. The method as claimed in claim 32, wherein Z is a hydrogen atom, Y is an alkyl group or an aryl group and wherein W is a phenyl group wherein at least one of the ortho-positions is substituted with a halogen atom.

34. The method as claimed in claim 33, wherein said coupler is 1-(2,4,6-trichlorophenyl)-3-{3-[(2,4-di-tert-amylphenoxy)-acetamido]-benzamido}-4-phenylsulfonamido-5-oxo-2-pyrazoline.

* * * * *